United States Patent
Gourmelon et al.

(10) Patent No.: US 10,456,089 B2
(45) Date of Patent: Oct. 29, 2019

(54) PATIENT MONITORING FOR SUB-ACUTE PATIENTS BASED ON ACTIVITY STATE AND POSTURE

(71) Applicant: KONINKLIJKE PHILIPS N.V., Eindhoven (NL)

(72) Inventors: Lena Gourmelon, Veldhoven (NL); Harald Greiner, Nufringen (DE); Stijn De Waele, Millwood, NY (US); Guenther Gegner, Tuebingen (DE); Teun Van Den Heuvel, Eindhoven (NL); Wilhelm Meier, Herrenberg (DE); Hanqing Cao, Mahwah, NJ (US); Thomas Gerhard Emmrich, Gaertringen (DE); Vincent Alexander Rudolf Aarts, Eindhoven (NL); Steffen Zimmermann, Dettenhausen (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 290 days.

(21) Appl. No.: 14/648,717

(22) PCT Filed: Dec. 13, 2013

(86) PCT No.: PCT/IB2013/060912
§ 371 (c)(1),
(2) Date: Jun. 1, 2015

(87) PCT Pub. No.: WO2014/091457
PCT Pub. Date: Jun. 19, 2014

(65) Prior Publication Data
US 2015/0305689 A1    Oct. 29, 2015

Related U.S. Application Data

(60) Provisional application No. 61/737,407, filed on Dec. 14, 2012.

(51) Int. Cl.
*A61B 5/00* (2006.01)
*A61B 5/0205* (2006.01)
(Continued)

(52) U.S. Cl.
CPC ............ *A61B 5/7285* (2013.01); *A61B 5/002* (2013.01); *A61B 5/0205* (2013.01); *A61B 5/11* (2013.01);
(Continued)

(58) Field of Classification Search
None
See application file for complete search history.

(56) References Cited

U.S. PATENT DOCUMENTS 5,593,431 A    1/1997    Sheldon
8,743,148 B2   6/2014    Gegner et al.
(Continued)

FOREIGN PATENT DOCUMENTS

JP    H1189802     4/1999
JP    H11155823    6/1999
(Continued)

OTHER PUBLICATIONS

Odell, M.; Are early warning scores the only way to rapidly detect and manage deterioration?; 2010; Nursing Times; 106(8)24-26.
(Continued)

*Primary Examiner* — Lindsey G Wehrheim
*Assistant Examiner* — Sana Sahand

(57) ABSTRACT

A method, and corresponding system (300), for monitoring patients based on activity state and posture. Activity state and/or posture of a patient are measured. Further, one or more vital signs of the patient are measured according to a schedule. Based on the measured activity state and/or pos-
(Continued)

ture of the patient and the measured one or more vital signs, the schedule is adjusted and/or patient deterioration is monitored for.

17 Claims, 16 Drawing Sheets

(51) Int. Cl.
    *A61B 5/11*     (2006.01)
    *G16H 50/30*     (2018.01)
    *G16H 50/20*     (2018.01)

(52) U.S. Cl.
    CPC ........... *A61B 5/1116* (2013.01); *A61B 5/1118* (2013.01); *A61B 5/4842* (2013.01); *A61B 5/7275* (2013.01); *A61B 5/7282* (2013.01); *A61B 5/7435* (2013.01); *G16H 50/20* (2018.01); *G16H 50/30* (2018.01); *A61B 5/746* (2013.01)

(56) References Cited

U.S. PATENT DOCUMENTS

| | | | |
|---|---|---|---|
| 2005/0215868 A1* | 9/2005 | Kenjou | A61B 5/0002 600/300 |
| 2009/0118595 A1 | 5/2009 | Greiner et al. | |
| 2010/0099954 A1 | 4/2010 | Dickinson et al. | |
| 2010/0298653 A1* | 11/2010 | McCombie | A61B 5/0002 600/301 |
| 2011/0066010 A1* | 3/2011 | Moon | A61B 5/0205 600/301 |
| 2011/0224500 A1 | 9/2011 | Banet et al. | |
| 2012/0136221 A1* | 5/2012 | Killen | G06F 19/3418 600/300 |
| 2012/0179067 A1 | 7/2012 | Wekell | |
| 2012/0190949 A1 | 7/2012 | McCombie et al. | |
| 2012/0290033 A1* | 11/2012 | Cho | A61N 1/056 607/20 |
| 2013/0137941 A1 | 5/2013 | Schardey | |
| 2013/0165800 A1* | 6/2013 | Shimizu | A61B 5/022 600/485 |
| 2013/0293373 A1 | 11/2013 | Gegner et al. | |
| 2013/0338543 A1 | 12/2013 | Gegner et al. | |

FOREIGN PATENT DOCUMENTS

| | | | |
|---|---|---|---|
| JP | 2007-229074 | 9/2007 | |
| WO | 2008045577 A2 | 4/2008 | |
| WO | 2011131612 A3 | 10/2011 | |
| WO | 2012117316 A2 | 9/2012 | |
| WO | WO 2012117316 * | 9/2012 | ............... A61B 5/00 |

OTHER PUBLICATIONS

Subbe, C. P., et al.; Validation of a modified Early Warning Score in medical admissions; 2001; Q J Med; 94:521-526.

\* cited by examiner

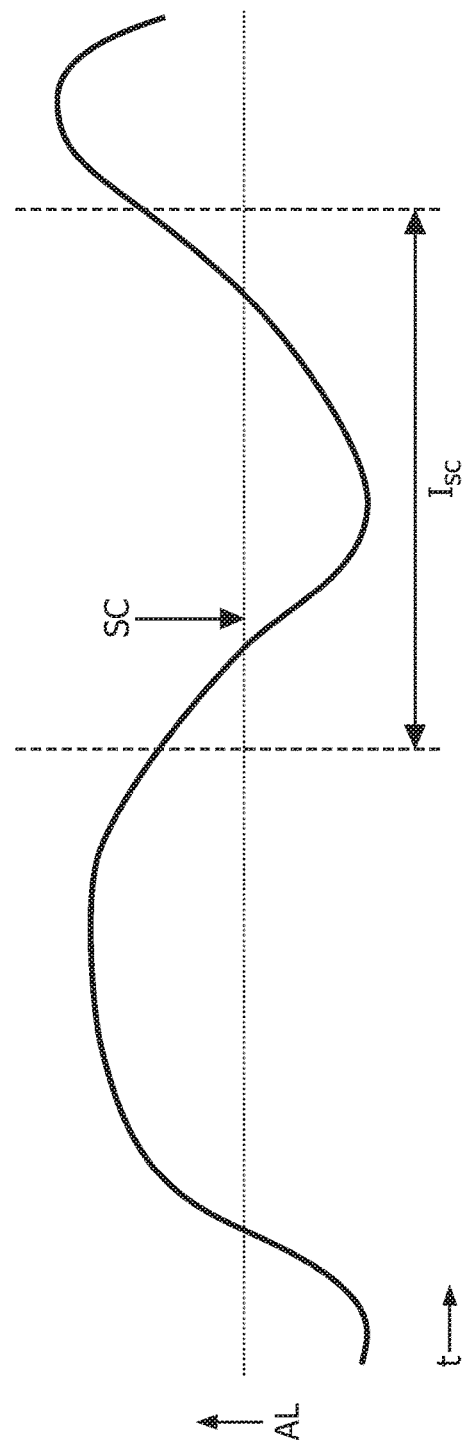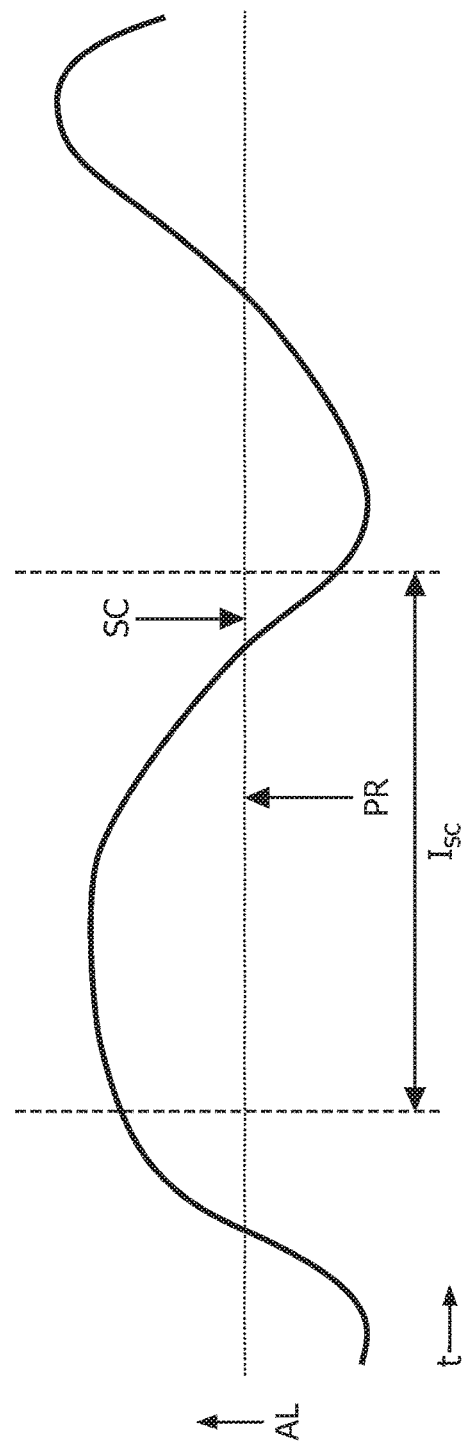

| Monitoring Frequency | 1 meas./ min | 1 meas./ 15 min | 1 meas./ 30 min | 1 meas./ h | 1 meas./ 30 min | 1 meas./ 15 min | 1 meas./ min |
|---|---|---|---|---|---|---|---|
| Score | 3 | 2 | 1 | 0 | 1 | 2 | 3 |
| Pulse rate | | <40 | 40-50 | 51-100 | 101-110 | 111-130 | >130 |
| Respiration rate | <9 | | | 9-14 | 15-20 | 21-30 | >30 |
| Oxygen saturation | | | | >94 | 90-94 | 88-90 | <88 |

| Time | Event |
|---|---|
| 8:00 | A patient is admitted on a medical floor. |
| 8:15 | A nurse connects the patient monitoring devices (e.g., for pulse rate, respiration rate, oxygen saturation) to the patient and performs an initial spot check. All the scores are 0 and the monitoring frequency for all the vital signs is 1 measurement per hour. |
| 9:15 | An automatic spot check is performed. All the scores are 0 and the monitoring frequency for all the vital signs is 1 measurement per hour. |
| 10:15 | An automatic spot check is performed. All the scores are 0 and the monitoring frequency for all the vital signs is 1 measurement per hour. |
| 11:15 | An automatic spot check is performed. All the scores are 0 and the monitoring frequency for all the vital signs is 1 measurement per hour. |
| 12:00 | An manual spot check is performed by the nurse. All the scores are 0. The nurse checks some other vital signs, such as temperature and how the patient is feeling. The next maual spot check is expected at 16:00. |
| 13:00 | An automatic spot check is performed. All the scores are 0 and the monitoring frequency for all the vital signs is 1 measurement per hour. |
| 14:00 | An automatic spot check is performed. Pulse rate increased and the pulse rate score is 1. All the other scores are still 0. The monitoring frequency for pulse rate is automatically increased to 1 measurement per minute and a measurement is made once at this monitoring frequency. The monitoring frequency for all the other vital signs is 1 measurement per hour. |
| 14:01 | An automatic spot check for verifying the pulse rate increase is performed. The pulse rate score is still 1, so a persistently higher pulse rate is confirmed. All the other scores are still 0. The monitoring frequency for pulse rate is automatically increased to 1 measurement per 30 minutes, whereas the monitoring frequency for all the other vital signs is 1 measurement per hour. |
| 14:31 | An automatic spot check is performed. Pulse rate decreased and the pulse rate score is 0. All the other scores are still 0. The monitoring frequency for pulse rate is automatically increased to 1 measurement per minute and a measurement is made once at this monitoring frequency. The monitoring frequency for all the other vital signs is 1 measurement per hour. |
| 14:31 | An automatic spot check for verifying the pulse rate decrease is performed. All the scores are still 0. The monitoring frequency for pulse rate is automatically decreased to 1 measurement per hour. The monitoring frequency for all the other vital signs is 1 measurement per hour. |
| 15:32 | An automatic spot check is performed. All the scores are 0 and the monitoring frequency for all the vital signs is 1 measurement per hour. |
| 16:00 | An manual spot check is performed. All the scores are 0. The nurse checks some other vital signs, such as temperature and how the patient is feeling. The next maual spot check is expected at 20:00. |

FIG. 10

| Time | Event |
|---|---|
| 13:00 | A patient comes back to a surgical floor after an operation. The patient is under patient controlled analgesia (PCA) |
| 13:10 | A nurse connects the patient monitoring devices (e.g., for pulse rate, respiration rate, oxygen saturation) and performs an initial spot check. All the scores are 0, but because the patient is under PCA, the patient is considered to have an increased risk of respiratory distress. Therefore the nurse sets the respiration rate monitoring frequency to 1 measurement per 15 minutes. All the other monitoring frequencies are 1 measurement per hour. |
| 13:25 | An automatic spot check for respiration rate is performed. Respiration rate is stable and the score is 0. |
| 13:40 | An automatic spot check for respiration rate is performed. Respiration rate decreased and the score is 0. |
| 13:55 | An automatic spot check for respiration is performed. Respiration rate decreased further (e.g., to less than 9 breaths per minute), and the respiration rate score increased to 3. The respiration rate frequency is increased to 1 measurement per minute. Further, an alert is sent to the nurse's pager. The monitoring frequency for all the other vital signs is set to 1 measurement per 15 minutes. |
| 14:05 | The nurse comes and checks the patient. Respiration rate is still too low with a score of 3. All the other vital signs are stable. The patient is taken out of PCA and analgesia is set to a lower dose. The monitoring frequency for respiration rate is 1 measurement per minute and the monitoring frequency of all the other vital signs is 1 measurement per 15 minutes. |
| 14:20 | The nurse comes to checks the patient again. Respiration rate slowly increases again but the respiration rate score is still 3. All the other vital signs are stable and the monitoring frequency of these vital signs stay unchanged. |
| 15:03 | The respiration rate is above a safe limit and the score is 0. The respiration rate frequency is automatically decreased to 1 measurement per hour.<br>All the other vital signs are stable and the monitoring frequency is automatically decreased to 1 measurement per hour. |

FIG. 11

| Key word or phrase | Icon | Icon (more abstract) |
|---|---|---|
| Supine | | |
| Prone | | |
| Lie on left side | | |
| Lie on right side | | |
| Invalid | -?- | |
| Key word or phrase | Icon | Icon (more abstract) |
|---|---|---|
| Upright | | |
| Reclined | | |
| Forward | | |
| Upside down | | |
FIG. 20
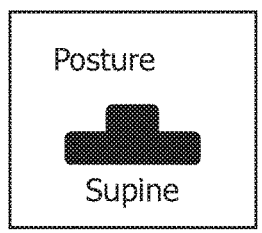
FIG. 21A
FIG. 21B

| Key word or phrase | Icon | Icon (more abstract) |
|---|---|---|
| Standing |  |  |
| Sitting |  |  |
| Walking |  |  |
| Running |  |  |
FIG. 22
```
Posture
11:20 Supine
12:30 Left side
13:40 right side
15:30 Prone
```
FIG. 23A
Posture
11:20
12:30
13:40
15:30
FIG. 23B
Posture
   
Time
FIG. 24

PATIENT MONITORING FOR SUB-ACUTE PATIENTS BASED ON ACTIVITY STATE AND POSTURE

CROSS REFERENCE TO RELATED APPLICATIONS

This application is a national filing of PCT application Serial No. PCT/IB2013/060912, filed Dec. 13, 2013, published as WO 2014/091457 A2 on Jun. 19, 2014, which claims the benefit of U.S. provisional application Ser. No. 61/737,407 filed Dec. 14, 2012, which is incorporated herein by reference.

The present invention relates generally to patient monitoring. It finds particular application in conjunction with patient monitoring for sub-acute patients based on activity state and posture and will be described with particular reference thereto. However, it is to be understood that it also finds application in other usage scenarios and is not necessarily limited to the aforementioned application.

In sub-acute hospital settings, 1-5% of patients experience Severe Adverse Events (SAEs) requiring ICU transfer, resuscitation or other rescue actions. Further, it is known that patient deterioration could be detected hours before these SAEs. Early Warning Scores (EWS) and Rapid Response Teams (RRT) are two combined mechanisms which have respectively been introduced to detect early signs of patient deterioration and act upon the early warnings to prevent SAEs.

Sub-acute care patients are typically monitored by intermittent, manual spot check measurements of vital signs. Common vital signs that are measured include pulse, oxygen saturation (SpO2), respiration, non-invasive blood pressure (NBP), temperature and carbon dioxide. These spot checks are performed at regular intervals, typically every 6-8 hours. The frequency depends on the severity of the patient and the number of staff. Further, to ensure adequate monitoring, requirements are put on the spot check schedule. An example requirement may be "The time between spot checks may not exceed 8 hours".

When using a EWS system, each of these vital sign measurements is translated in a score, which are summed-up to give a total score related to the condition of the patient. An increasing score provides an early warning of patient deterioration. Often, when the nurse feels that the patient is worsening or needs closer attention, they increase the frequency of spot checks. Further, the nurse may use monitoring devices for automatic spot check measurements between consecutive manual spot checks. This is advantageous because a patient could deteriorate between two consecutive spot checks, effectively leading to delays in detection and therefore increased risk for the patient.

One challenge with manual spot checks is that manual spot checks pose a large work load for nurses. Further, with spot checks, it's important to make sure that the patient has been at rest for some time before performing the measurements in order to ensure that the results reflect the patient's baseline situation rather than natural fluctuations related to physical activity or variation in posture. In view of this, another challenge with manual spot checks is that nurses taking vital signs may not properly ensure that the patient is in the correct (resting) state before obtaining the vital signs.

The foregoing challenges regarding manual spot checks are exacerbated by increased pressure for cost reduction of healthcare, which is leading to more and older patients, less staff, less educated and qualified staff and patients that are transferred earlier from the intensive care unit (ICU) to the general ward. Hence, there is a trend towards automated, unattended spot checks.

Monitoring devices including sensors that are continuously connected to the patient can perform unattended monitoring. Monitoring devices for the sub-acute hospital settings should be different from acute hospital settings in several aspects. Monitoring devices should enable ambulatory monitoring. Sub-acute care patients should not be restricted in their mobility and should be able to walk around. Wireless monitoring devices are therefore preferred. Due to a low nurse to patient ratio, monitoring devices should require minimal maintenance by nurses. Monitoring devices should submit reliable and actionable information, avoiding unmanageable overflow of false and/or irrelevant alerts.

A typical sampling scheme for these monitoring systems and/or devices is to measure at a fixed sampling interval, such as every six hours, corresponding to the spot check interval. While higher sampling rates are possible, low sampling rates may be preferred to increase battery life of wireless monitoring systems and/or devices. Further, general ward patients are generally less at risk than ICU patients, so low sampling rate is typically sufficient. Alternatively, these monitoring systems and/or devices can be employed to measure at a fixed sampling interval between manual spot checks.

One challenge with unattended spot checks is that measurements may not be comparable due to, for example, measurements taken across different patient states (e.g., walking versus in bed). This is likely to occur in general ward patients wearing wireless monitoring systems and/or devices. Measurements taken while the patient is in different states may result in inaccuracies in derived results, such as scores (e.g., early warning score (EWS)), and automatically detected patient deteriorations, as well as an increased number of irrelevant alerts. For example, a patient's heart rate may be high because the patient has just climbed the stairs. This would lead to a clinically meaningless alert for high heart rate.

One approach for addressing this challenge is to correct alarm thresholds based on the activity level of a patient, for example, derived from an accelerometer. However, in practice, it is very difficult to reliably adjust the alarm thresholds based on the activity level. For example, drawing on the above example, the relation between activity level and heart rate is not very stable. It varies strongly with disease conditions, as well as between patients, and depends on the activity type, which is hard to derive from an accelerometer.

Another challenge with unattended spot checks is the spot checks may occur when the patient is asleep. This may disturb the patient's sleep and have an adverse effect on the patient's recuperation. Automated blood pressure measurements are especially likely to disturb a patient's sleep.

Another challenge with unattended spot checks is the frequency with which the spot checks are performed. Not every patient requires the same level of monitoring. For patients at risk of deterioration, certain vital signs need to be measured more frequently. To make sure the deteriorating patients are properly monitored, one approach is to configure the monitoring devices to measure at a high sampling frequency for all patients. However, there are a number of disadvantages to this approach.

Blood pressure measurements are obtrusive for patients, since such measurements involve inflation of an arm cuff. This can leave patients uncomfortable, thereby reducing patient satisfaction and slowing patient recovery. Further, the increased monitoring frequency reduces battery life of monitoring devices. This results in an increased work load for the nurses, as batteries need to be replaced more frequently. Even more, the work load for re-application of sensors that have fallen off or have a bad contact ($SpO_2$, ECG) increases because sensors need to be applied more frequently when the monitoring schedule requires frequent sampling.

Also, a system with a high monitoring frequency may produce an unacceptably high number of false alerts. This is due to the fact that the majority of the sub-acute ward patients have a stable condition and only a small percentage of them will be experiencing deterioration. Possible solutions that can be used to continue sampling the vital signs at a high frequency include averaging the samples over a long period of time to be more accurate, or modifying thresholds and introducing reconfirmation measurements.

Another approach to setting the spot check frequency is for the nurses to manually select an appropriate sampling rate per patient, dependent on the patient condition. However, with the low nurse to patient ratio, this results in a significant work load for nurses. This is aggravated by the fact that the patient status can change over time. A patient who looks stable at admission may turn unstable over time. This implies that regular attention from the nurse is needed.

As the spot check measurements themselves are being automated, there is a need to also automate the verification of a base-line situation. A well-known method for this is the use of motion sensing (e.g., through accelerometry or video actigraphy). See, for example, U.S. Pat. No. 5,593,431, which describes motion sensing using an accelerometer. For assessment of mental aspects of activity state, such as sleep detection, methods such as those based on electroencephalography (EEG) may be used (e.g., as described in U.S. Patent Application Publication No. 2010/0099954). Furthermore, information on patient activity may be obtained by means of automatic interaction with the patient (e.g., through an electronic questionnaire).

The present invention provides new and improved methods and systems which overcome the above-referenced problems and others.

In accordance with one aspect, a medical system is provided. At least one processor is programmed to measure activity state and/or posture of a patient and measure one or more vital signs of the patient according to a schedule. Based on the measured activity state and/or posture of the patient and the measured one or more vital signs, the at least one processor is further programmed to at least one of adjust the schedule and monitor for patient deterioration.

In accordance with another aspect, a medical method is provided. Activity state and/or posture of a patient are measured, and one or more vital signs of the patient are measured according to a schedule. Based on the measured activity state and/or posture of the patient and the measured one or more vital signs, the schedule is adjusted and/or patient deterioration is monitored for.

In accordance with another aspect, a medical system is provided. A patient preparation system is configured to prepare a patient for automatic spot-checks using activity state and/or posture of the patient. An adaptive patient monitoring system is configured to adjust one or more monitoring frequencies of the automatic spot checks using vital sign measurements of the patient and monitor for patient deterioration based on vital sign measurements of the patient and activity state and/or posture of the patient.

In accordance with another aspect, an adaptive patient monitoring system includes a score processing system. The scoring scheme for a patient can include vital sign thresholds and a list of measured vital signs. The adaptive patient monitoring system can be configured to adjust the scoring scheme based on vital sign measurements of the patient and activity state and/or posture of the patient.

One advantage resides in more reliable monitoring of patients.

Another advantage resides in reduced work load for nurses.

Another advantage resides in monitoring devices that enable ambulatory monitoring.

Another advantage resides in monitoring devices that require minimal maintenance.

Another advantage resides in unobtrusive monitoring of patients.

Another advantage resides in monitoring which takes into account patient state.

Another advantage resides in improved patient deterioration detection.

Another advantage resides in describing dependencies of vital signs measurements and patient activity and/or posture.

Another advantage resides in simplifying clinical workflow and judgments of patient conditions.

Another advantage resides in reducing misinterpretations of vital signs and misjudgments of patient conditions.

Still further advantages of the present invention will be appreciated to those of ordinary skill in the art upon reading and understanding the following detailed description.

The invention may take form in various components and arrangements of components, and in various steps and arrangements of steps. The drawings are only for purposes of illustrating the preferred embodiments and are not to be construed as limiting the invention.

FIG. 7A illustrates an example of spot check timing management.

FIG. 7B illustrates another example of spot check timing management.

FIG. 10 illustrates an example scenario to which an adaptive patient monitoring system can be applied.

FIG. 11 illustrates another example scenario to which an adaptive patient monitoring system can be applied.

FIG. 20 illustrates a table of key words or phrases and corresponding icons that can be used to describe posture.

FIG. 21A illustrates an example display of posture.

FIG. 21B illustrates another example display of posture.

FIG. 22 illustrates a table of key words or phrases and corresponding icons that can be used to describe dynamic posture.

FIG. 23A illustrates an example list of keywords or phrases, and corresponding timestamps, for posture.

FIG. 23B illustrates an example list of icons, and corresponding timestamps, for posture.

FIG. 24 illustrates an example timeline for posture.

While motion sensing can passively verify whether or not the patient is and/or has been at rest, it still lacks a nurse's capability to actively instruct the patient to go into a resting state. The present invention provides a system and method to enable this in an automatic system, so that time-consuming spot checks as traditionally performed by nurses can indeed be fully automated.

Figure 1:
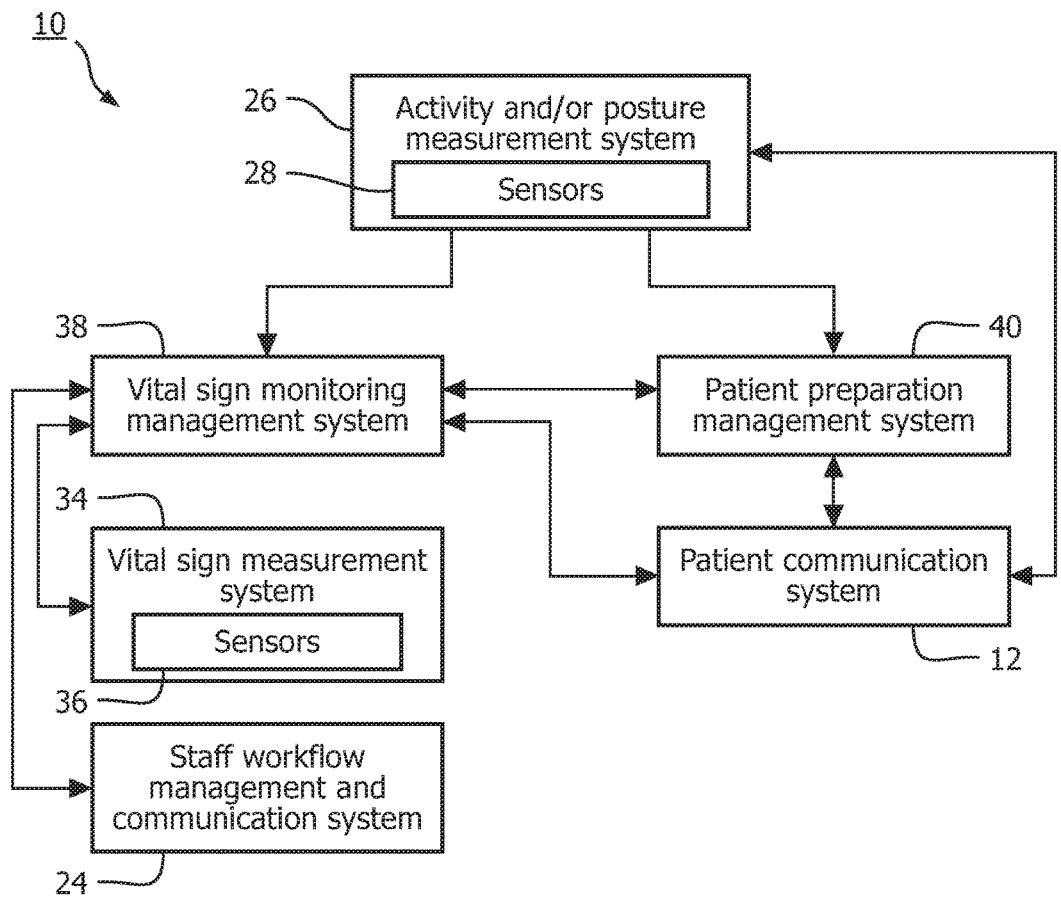
FIG. 1 illustrates a patient preparation system for smart intermittent vital sign monitoring.

With reference to FIG. 1, a patient preparation system 10 for smart intermittent vital sign monitoring is provided. The patient preparation system 10 is typically employed in situations where patients can be expected to be mobile and responsive to automated instructions. General (low-acuity) hospital wards are a prominent example.

A patient communication system 12 allows unidirectional and/or bidirectional communication between the patient preparation system 10 and an associated patient. The patient communication system 12 can be realized by, for example, a conventional display system, a touch-screen system, a sound playing system, a lighting system, a tactile interface system, or a combination of any or all of such systems.

The patient communication system 12 receives requests and/or messages for the patient from other systems of the patient preparation system 10. For example, the patient communication system 12 could receive a request for an at-rest patient to maintain a resting position for an indicated (and dynamically updated) period of time until vital sign measurements are completed. In response to a patient request and/or message, a patient interface 18 (see FIG. 2) of the patient communication system 12 is employed to prompt the patient and, in some instances, receive request information. The patient interface is, for example, one or more uni- or bi-directional communication means, such as audio systems, lighting systems, display systems, touch-screen systems, buzzer systems, etc. The patient interface could further include environmental aspects, such as curtains, windows, doors, etc.

Figure 2:
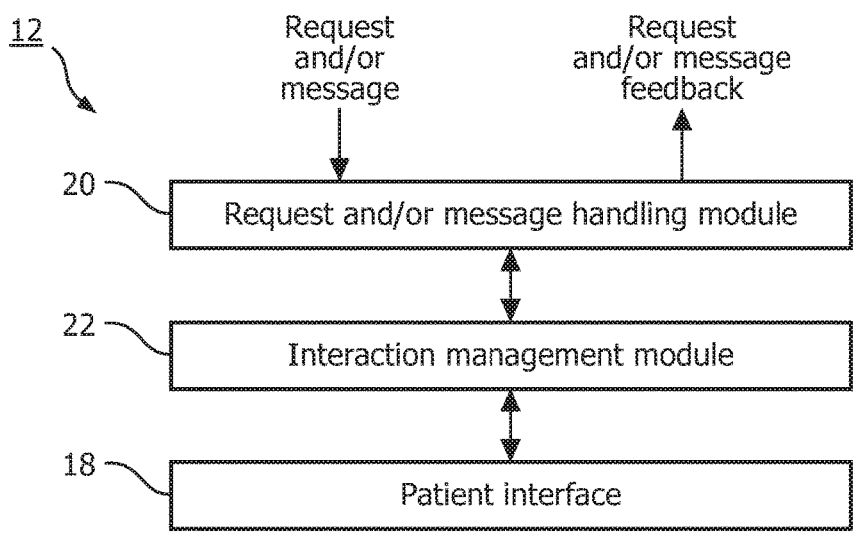
FIG. 2 illustrates a patient communication system.

With reference to FIG. 2, an example of the patient communication system 12 is illustrated. A request and/or message handling module 20 receives requests and/or messages. These requests and/or messages are translated into instructions to an interaction management module 22, which controls the patient interface 18 in accordance with the instructions. The interaction management module 22 can receive feedback from the patient interface 18, which is passed back to the request and/or message handling module 20.

Referring back to FIG. 1, a staff workflow management and communication system 24 allows unidirectional and/or bidirectional communication between the patient preparation system 10 and staff at a medical institution, such as a hospital, employing the patient preparation system 10. Communication can be performed using, for example, one or more uni- or bi-directional communication means, such as audio systems, lighting systems, display systems, touch-screen systems, buzzer systems, etc. Further, the staff workflow management and communication system 24 can allow modification of staff workflows. For example, the workflow of a nurse could be modified to increase the frequency of spot checks.

An activity and/or posture measurement system 26 measures the activity state and/or posture of the patient. Activity can include one or more of present and recent physical activity levels, physical activity types, sleep state(s), mental state(s), and so on. A primary example of an activity state is a resting state (i.e., a state in which a patient's vital signs are likely to reflect a baseline situation). Posture can include, for example, supine and prone.

The activity state and/or posture can be determined automatically using one or more sensors 28 according to well-known techniques. For example, physical aspects of the activity state of the patient can be determined using motion sensing with, for example, accelerometry or video actigraphy. Mental aspects of the activity state can be determined using, for example, sleep detection methods, such as those based on electroencephalography (EEG). Additionally, the activity state and/or posture can be determined using the patient communication system 12 and/or the staff workflow management and communication system 24. For example, the activity state and/or posture can be obtained by means of automatic interaction with the patient (e.g., through an electronic questionnaire). As another example, the activity state and/or posture can be obtained from nurses performing spot checks.

Figure 3:
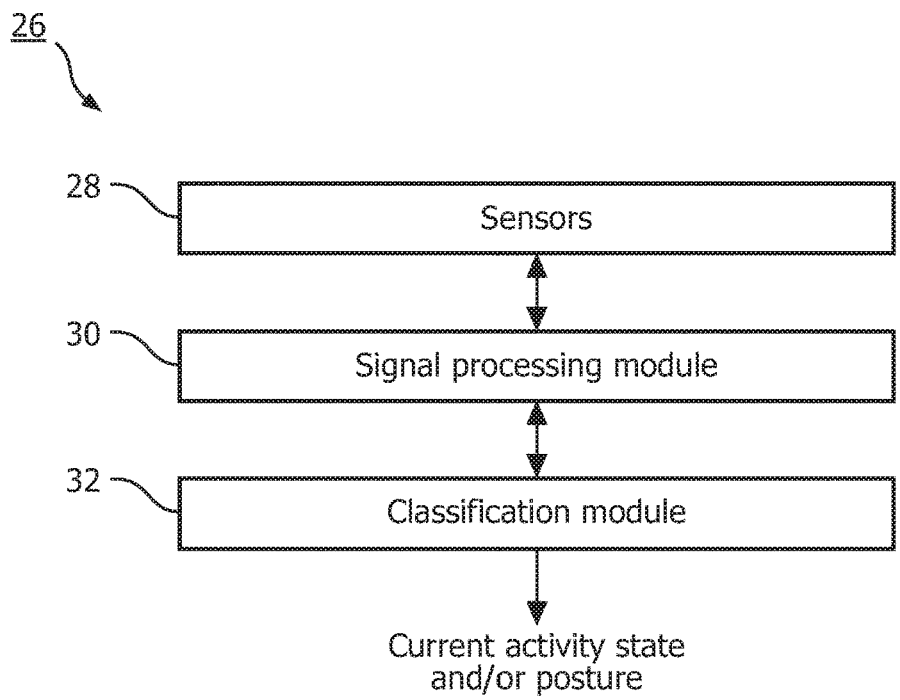
FIG. 3 illustrates an activity and/or posture measurement system.

With reference to FIG. 3, one embodiment of the activity and/or posture measurement system 26 is provided. The patient activity state monitoring system receives signals from the sensors 28, which are processed by a signal processing module 30. The signal processing module 30 extracts features from the signals, which are used by a classification module 32 to classify the activity state and/or posture of the patient. The features can include, for example, acceleration.

Referring back to FIG. 1, a vital signs measurement system 34 automatically measures one or more vital signs using one or more sensors 36. These sensors 36 can overlap with sensors 28 employed for determining activity state and/or posture. The vital signs can include, for example, one or more of pulse, oxygen saturation (SpO2), respiration, non-invasive blood pressure (NBP), temperature and carbon dioxide. Measurements are typically performed periodically according to a schedule. For example, measurements could be performed periodically every hour. Further, measurement schedules can be configured individually for each vital sign, globally for all vital signs, or individually for sets of vital signs. For example, NBP can be measured every 4 hours, SpO2 can be measured every 1 hour, and respiration can be measured every 15 minutes.

A vital sign monitoring management system 38 intelligently performs spot checks on the patient (i.e., collects vital sign measurements) when the activity state and/or posture of the patient is in a required activity state and/or posture, such as a baseline state (e.g., resting state). Vital sign measurements can be collected automatically from the vital signs measurement system 34, the staff workflow management and communication system 24, the patient communication system 12, or any other system of the patient preparation system 10. For example, staff can be requested to take vital signs measurements. In addition, if a patient is not in a required activity state and/or posture after a certain amount of time (i.e., convenience period), the vital sign monitoring management system 38 can interact with one or more of the vital signs measurement system 34, the staff workflow management and communication system 24, the patient communication system 12, or any other system of the patient preparation system 10 to address the situation.

The vital sign monitoring management system 38 receives input on the current activity state and/or posture of the patient from the activity and/or posture measurement system 26 and monitoring settings from the staff workflow management and communication system 24. Monitoring settings can specify one or more of spot check frequency, the required activity state and/or posture of the patient, a spot check interval within which spot checks need to be performed, and the like. The spot check frequency is typically set based on hospital policy and/or the severity of the patient. Further, the spot check frequency can be individually set for the vital signs. The spot check interval provides a margin around a scheduled spot-chock within which to perform the spot check. Further, the spot check interval can, for example, be centered around the scheduled time for a spot check. To illustrate, suppose a spot check is scheduled for 2 PM and a spot check interval of 40 minutes is centered around this scheduled spot check. In this example, the spot check can be performed from 1:40 PM to 2:20 PM.

Using the current activity state and/or posture of the patient and the monitoring settings, the vital sign monitoring management system 38 attempts to take vital sign measurements according to the spot check frequency. From the beginning to the end of a spot check interval of a scheduled spot check, the vital sign monitoring system 38 monitors for the current activity state and/or posture to match the required activity state and/or posture. If a match is found, vital sign measurements are collected, typically automatically using the vital signs measuring system 34. If no vital sign measurements are collected before the end of the spot check interval, the staff can be alerted to the absence of a measurement using the staff workflow management and communication system 24.

After a predetermined amount (e.g., a percentage) of the spot check interval has elapsed without collecting measurements, a patient preparation management system 40 can be employed to instruct the patient to take the required activity state and/or posture. For example, the patient can be instructed to get in a resting position. The percentage could be, for example, 0% (i.e., always instruct the patient) or 50% (i.e., after half of the spot check interval has elapsed).

The patient preparation management system 40 receives the required activity state and/or posture and the time period within which to instruct the patient (i.e., the current time to the end of the spot check interval). Further, the patient management system 40 receives the current activity state and/or posture of the patient. Based on the inputs, the patient communication system 12 is controlled to instruct the patient. The instruction is typically by one or more of a display, light, sound, and buzzer aimed at the particular patient, for example, embedded within the sensors 28 and/or the of the activity and/or posture measurement system 26. If the patient has achieved the required activity state and/or posture or the spot check interval ends, the instructions to the patient are disabled.

Figure 4:
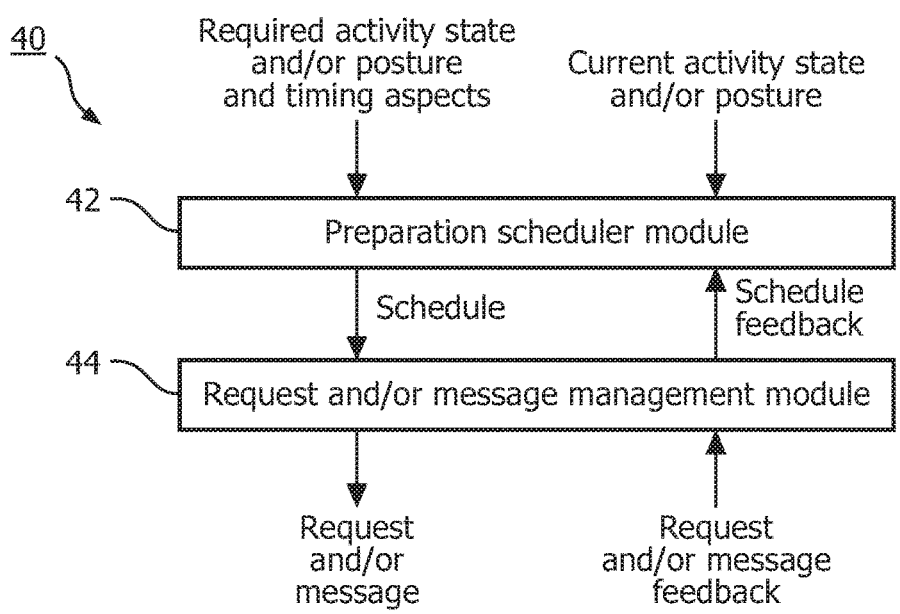
FIG. 4 illustrates a patient preparation management system.

With reference to FIG. 4, one embodiment of the patient preparation management system 40 is illustrated. A preparation scheduler module 42 uses the current activity state and/or posture, as well as the required activity state and/or posture and timing aspects, to establish a patient preparation schedule. This schedule is fed to a request and/or message management module 44, which translates the schedule to individual preparation requests and/or messages that can be handled by the patient communication system 12. The request and/or message management module 44 can receive feedback on the handling of the requests and/or messages, which can in turn be used to provide feedback to the preparation scheduler module 42.

Figure 5:
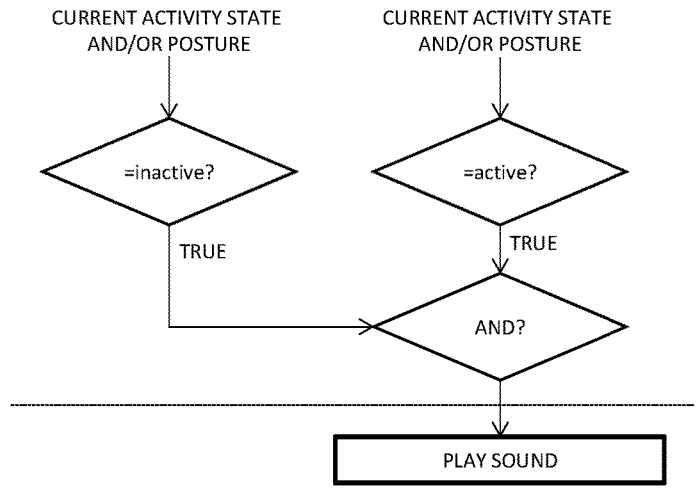
FIG. 5 illustrates the functionality of a combination of a patient preparation management system and a patient communication system.

With reference to FIG. 5, a flowchart illustrates the functionality of a combination of the patient preparation management system 40 and the patient communication system 12 according to one embodiment. The detections above the dotted line are performed by the patient preparation management system 40 and the action below the dotted line is performed by the patient communication system 12. When the current activity state and/or posture of the patient indicates the patient is active and the required activity state and/or posture is that the patient is inactive, the patient communication system 12 is employed to play a sound. For example, the sound could notify the patient to go to bed.

Referring back to FIG. 1, in order to optimize a patient's sleep quality, the patient preparation management system 40 can avoid disturbances from either clinician visits or automatic measurements (e.g., an automatically inflated cuff for non-invasive blood pressure measurement) when the current activity state and/or posture of the patient indicates the patient is sleeping. Spot check frequencies and/or schedules of non-disturbing vital signs could be adjusted and/or increased to bridge the gap of suppressed vital signs (e.g., pulse can be determined from SpO2 instead of NBP).

Further, depending on available monitoring technology and existing working practices, it may sometimes be necessary to have a clinician perform at least some vital sign measurements by hand. In this case, the patient activity state needs to match the clinician's workflow as well as possible in order to achieve optimal efficiency. The patient preparation management system 40 can address this using a combined approach. Patients can be instructed to attain the required activity state and/or posture using the patient preparation management system 40, and the clinician workflow schedule can be adapted dynamically depending on actual patient activity state and/or posture using the clinician workflow management and communication system 24.

To illustrate, suppose a patient is sleeping while his vital signs need to be measured by a nurse with only moderate urgency. The nurse's workflow schedule can be adapted to let the patient sleep while the nurse first attends to other duties (e.g., measuring vital signs on already awake patients).

Figure 6:
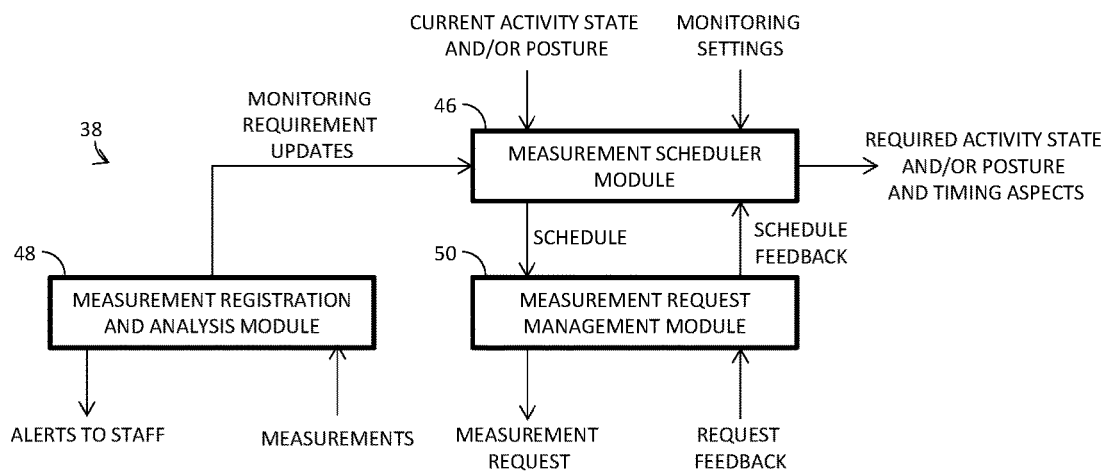
FIG. 6 illustrates a vital sign monitoring management system.

With reference to FIG. 6, one embodiment of the vital sign monitoring management system 38 is illustrated. A measurement scheduler module 46 receives the current activity state and/or posture and the monitoring settings, as well as updates from a measurement registration and analysis module 48 and schedule feedback from a measurement request management module 50. Based on this input, the measurement scheduler module 46 generates a schedule (or individual schedules for the vital signs), which is provided to the measurement request management module 50. Further, the measurement schedule module 46 provides the required activity state and/or posture, as well as timing information to the patient preparation management system 40.

The measurement request management module 50 attempts to collect vital sign measurements from the vital signs measurement system 34 and/or the clinician workflow management and communication system 24 in accordance with the measurement schedule. Feedback from the measurement request management module 50 is provided to the measurement scheduler module 46 describing the attempt to collect vital sign measurements.

The measurement registration and analysis module 48 receives vital sign measurements from the vital signs measurement system 34 and/or the staff workflow management and communication system 24. Based thereon, an analysis is performed to assess whether any patient alerts need to be generated. Alerts can be provided to staff by way of the staff workflow management and communication system 24. Further, updates to the monitoring settings used by the measurement scheduler module 46 can be made. For example, if the analysis of the vital sign measurements indicates that a patient is deteriorating, the frequency of spot checks can be increased.

Referring to FIGS. 7A and 7B, two examples of spot check timing management according to patient preparation system 10 are illustrated. In the illustrated examples, the required activity state and/or posture is a low activity level. Further, the solid lines represent some activity level signal, and the dotted line correspond to the maximum activity level for spot check measurements. "AL" corresponds to activity level, "t" corresponds to time, "PR" corresponds to preparation request, "SC" corresponds to spot check, and "$I_{sc}$" corresponds to spot check interval.

In the example of FIG. 7A, a spot check interval (i.e., a time span within which a spot check measurement needs to be performed) coincides with a 'resting' period, so the spot check can be performed shortly after the activity level has dropped below the maximum allowed level. In the example of FIG. 7B, the patient activity level is too high for a spot check measurement during the initial part of the defined interval, so the patient is instructed to go into a resting state. In response to the instructions, the patient goes into a resting state (i.e., activity level drops below the maximum allowed level) and a valid spot check measurement can be performed within the required spot check interval. Note that in these examples, the patient is only instructed when it appears necessary to make a valid spot check measurement, as is the case in the example of FIG. 7B.

Similar to a nurse adapting the frequency of spot checks to the patient condition, the present invention provides a system and method to adapt the monitoring scheme to the condition of the patient. This is achieved by automatically increasing the monitoring frequency in case of worsening of the patient condition in order to ensure timely alerting and tracking of further deterioration.

Figures 8, 9:
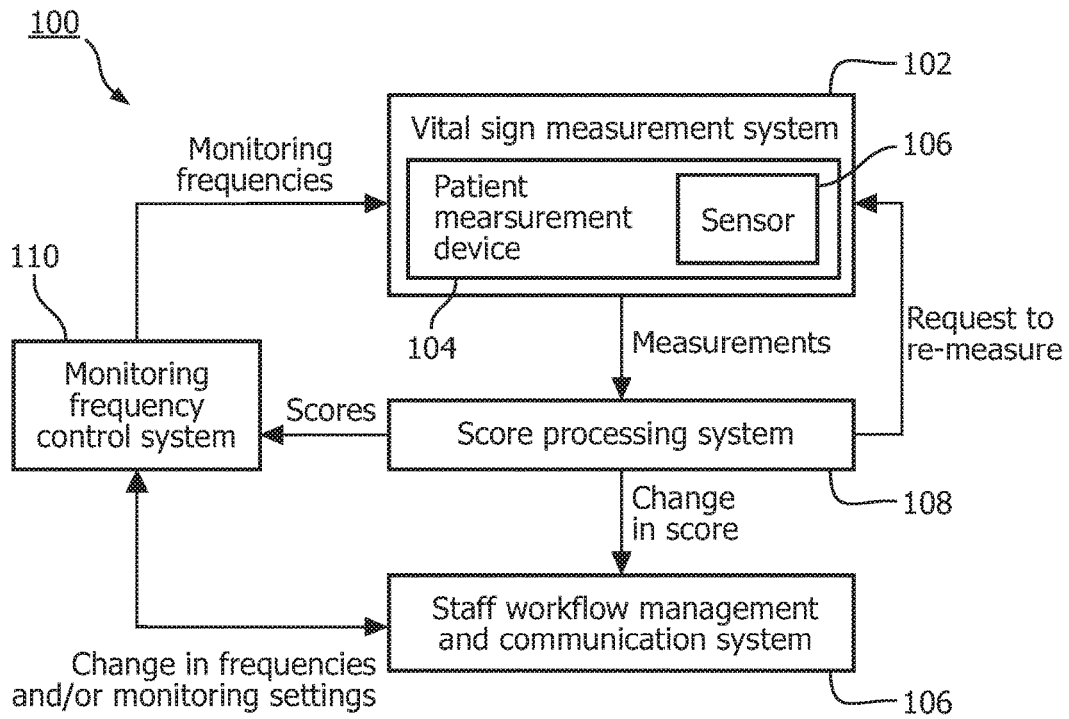
FIG. 8 illustrates an adaptive patient monitoring system.
FIG. 9 illustrates an example of adjusting monitoring frequency based on a three parameter Early Warning Score (EWS) system.

With reference to FIG. 8, an adaptive patient monitoring system 100 is provided. As above, with the patient preparation system 10, the adaptive patient monitoring system 100 is typically employed in situations where patients can be expected to be mobile. General (low-acuity) hospital wards are a prominent example.

The adaptive patient monitoring system 100 includes a vital signs measurement system 102 performing automatic spot checks on the patient (i.e., collecting vital sign measurements). The vital signs can include, for example, one or more of pulse, oxygen saturation, respiration, non-invasive blood pressure, temperature and carbon dioxide. To facilitate the automatic spot checks, the vital signs measurement system 102 includes one or more patient measuring devices 104 measuring vital signs of the patient using one or more sensors 106.

The patient measuring devices 104 are typically positioned on, within, or proximate to the patient. Further, the patient measuring devices 104 are typically wireless to allow ambulatory movement of the patient. The vital signs are measured at a minimum frequency, which ensures sufficient coverage between two manual, consecutive spot checks by a clinician. For example, if manual spot checks are performed every 4 hours, automatic spot checks can be performed every hour between the manual spot checks or individual vital sign schedules can be set, such as NBP every hour and SpO2 every 15 minutes.

A staff workflow management and communication system 106 allows unidirectional and/or bidirectional communication between adaptive patient monitoring system 100 and staff at a medical institution, such as a hospital, employing adaptive patient monitoring system 100. Communication can be performed using, for example, one or more uni- or bi-directional communication means, such as audio systems, lighting systems, display systems, touch-screen systems, buzzer systems, etc. Further, the staff workflow management and communication system 106 can allow modification of staff workflows. For example, the workflow of a nurse could be modified to increase the frequency of spot checks.

A score processing system 108 estimates the patient condition based on all vital sign measurements received from the vital signs measurement system 102. For example, a score could be assigned to each vital sign and then the scores of the vital signs could be totaled to determine a total monitoring score indicative of the patient condition. In some embodiments, the vital sign measurements are obtained from the patient preparation system 10 of FIG. 1.

If the patient's score for one or more vital signs has become worse, and/or improved, compared to the previous spot check, the score processing system 108 automatically re-measures these vital signs and/or other vital signs (e.g., using the vital signs measurement system 102b after a delay, such as one, five, ten or fifteen minutes. This ensures that the condition is not temporary or due to artifact. If an increase in a score persists, a monitoring frequency control system 110 automatically increases the automatic spot check frequency for the vital sign, a subset of vital signs or all the vital signs. Similarly, if a decrease in a score persists, the monitoring frequency control system 110 automatically decreases the automatic spot check frequency for the vital sign, a subset of vital signs or all the vital signs.

The monitoring frequency control system 110 controls the spot check frequencies in accordance with monitoring settings and the scores determined by the score processing system 108. The monitoring settings can specify one or more of limits (upper and/or lower) on the monitoring frequencies of the vital signs, default monitoring frequencies for the vital signs, and the like. Further, the monitoring settings can be specified based on, for example, clinician input (e.g., from the staff workflow management and communication system 106), policy of the medical institution employing the adaptive patient monitoring system 100, patient condition, and the like.

As to clinician input, when a clinician performs a manual spot check, the time and vital sign measurements can be provided to the monitoring frequency control system 110. In this way, the time of the next expected manual spot check is known and can be used to decide when to notify a clinician, as described below. In addition, clinicians can set a monitoring frequency they think appropriate. For example, suppose a patient has been given some medication, thereby leading to increased heart rate. Because the clinician knows about this medication, the clinician can set the monitoring frequency to 1 measurement per hour and override a monitoring frequency of 1 measurement per 30 minutes that the monitoring frequency control system 110 would otherwise use.

When automatically varying the spot check frequency of a vital sign due to, for example, deterioration of the vital sign, the new spot check frequency will depend on the patient's condition. For example, there could be four different automatic monitoring frequencies: 1) 1 measurement per hour; 2) 1 measurement per 30 minutes; 3) 1 measurement per 15 minutes; and 4) 1 measurement per minute, each corresponding to a score or score range. The worse the patient's score is, the higher the monitoring frequency.

The frequency of each vital sign is typically adapted independent of the others and based on the individual score for the vital sign. However, the frequency of each vital can be dependent of the others and based on the total score. For example, all the vital signs can share a common frequency based on the total score. As another example, if the total score is high, the spot check frequency of each parameter can be increased one or more levels (e.g., from 1 measurement per hour to 1 measurement per 15 minutes) from what it would be if set independent of the other vital signs. Otherwise, the frequency of each vital sign is independently set. The total score is high when the total score exceeds a threshold set by the operator of the adaptive patient monitoring system 100, the threshold deemed to indicate a high total score by the operator.

Further, when the adaptive patient monitoring system 100 is initialized, a first set of measurements is performed. The first set of measurements are used by the score processing system 108 and the monitoring frequency control system 110 to determine the baseline monitoring score and to choose the baseline monitoring frequency, respectively.

The monitoring frequency control system 110 and/or the score processing system 108 can be employed to notify a clinician of a change in spot check frequency and/or a change in score, respectively, which is clinically significant. A clinically significant change can be one in which the extent of the change exceeds a threshold set by an operator of the adaptive patient monitoring system 100, the threshold indicative of a clinically significant change. Even more, a nurse can be notified to one or more of add additional patient measuring devices, perform a spot check, and check other vital signs (e.g., consciousness) by, for example, the monitoring frequency control system 110. Notifications can be conveyed to a clinician using the staff workflow management and communication system 106. For example, a message can be displayed on a preferred interface, such as, for example, a central station or a nurse call or paging device.

Referring to the table of FIG. 9, an example of how the monitoring frequency could be automatically adjusted based on a three parameter Early Warning Score (EWS) system. The table shows the relationship between monitoring frequency, vital sign measurement, and individual score. The monitoring frequency can be either coupled independently to each vital signs score or to the total EWS. In the first case, each vital sign will have a particular monitoring frequency linked to the corresponding vital sign score. In the second case, all vital signs will have the same monitoring frequency corresponding to a certain EWS.

Assuming all vital signs have the same monitoring frequency, suppose the total EWS score is greater than or equal to 3. In such a case, the minimum monitoring frequency of 1 measurement/15 minutes is employed. If any of the individual scores increase, the corresponding measurement is repeated after a delay (e.g., of 1 minute or 5 minutes) to ensure this condition persists. If the condition persists, a notification is sent to a clinician and the monitoring frequency is increased based on the table of FIG. 9. Otherwise, this temporary patient worsening may be discarded and the monitoring frequency remains unchanged.

Referring to FIG. 10, a table of an example scenario to which the adaptive patient monitoring system 100 can be applied is provided. As can be seen, at 14:00 pulse rate increased and at 14:31 pulse rate decreased. The temporary increase in pulse rate may have been caused by some sustained effort from the patient and was not clinically relevant. The adaptive patient monitoring system 100 adjusted the sampling frequency automatically to ensure a safe monitoring of the patient. The pulse rate monitoring frequency was automatically switched back to the minimum monitoring frequency when the patient's pulse rate was back to normal to reduce power consumption for the patient measuring devices 104. No notification message of the monitoring frequency increase for pulse rate was sent to the nurse because no action was further required from the nurse. In order to avoid overloading clinicians with non-clinically relevant information, only changes in patient condition which would require action from clinicians are notified to them. One method to achieve this behavior of the scoring system 108 is the request to re-measure and therefore reassure the deteriorating condition. On the other hand, in case activity information is available to the scoring system 108, the scoring system 108 can suppress re-measurement, and notify immediately, if an activity is within acceptable range.

Referring to FIG. 11, a table of another example scenario to which the adaptive patient monitoring system 100 can be applied is provided. At 13:55, the patient experienced a critical situation with a respiration rate abnormally low due to a high dose of analgesia that was too high. The nurse knew that the patient was at risk of respiratory distress due to patient-controlled analgesia (PCA) and therefore set a higher monitoring frequency for the respiration rate. The adaptive patient monitoring system 100 adapted the monitoring frequency further to the highest level of the monitoring frequency when the respiration rate degraded further. The nurse was alerted about the patient's condition because this situation required quick action from her.

Referring back to FIG. 8, the monitoring frequency control system 110 can additionally or alternatively employ other approaches to adapt the monitoring frequencies of the vital signs. One such approach builds on the realization that hospital work flow often prescribes that manual spot checks should be performed at an increased frequency when there is a concern for patient deterioration. Accordingly, the automatic spot check frequency can be increased for patients that have a higher manual spot check frequency. For example, the automatic spot check frequency can be adjusted in linear proportion to the manual spot check frequency. This approach can complement the above described approach in that it can adjust the automatic spot check frequency for patients where potential deterioration is derived by the staff from information outside of the measured vital signs.

Another approach builds on the realization that hospital workflow may prescribe that an acuity level is set for each patient. For example, green could be used to indicate the patient is stable and/or low risk, whereas red could be used to indicate the patient is at high risk. This indicator is typically used to adjust manual spot check frequency, and can similarly be used to adjust automatic spot check frequency.

Another approach of the adaptive patient monitoring system 100 is to reconfigure the scoring scheme assigned to the patient. The patient individual scoring scheme can include vital sign thresholds and a list of measured vital signs. The adaptive patient monitoring system 100 can be configured to adjust the individual scoring scheme based on vital sign measurements of the patient and activity state and/or posture of the patient.

The present invention includes a system and method in which the additional available patient information of activity state and posture are used to enhance the validity and quality of vital sign measurements and derived results, such as scores. Measurement relevance indicators based on activity state and posture can be used to describe dependencies of vital signs measurements and patient activity state and/or posture. Further, vital sign measurements can be collected based on activity state and/or posture, and notifications can be generated based on activity state and/or posture.

Figure 12:
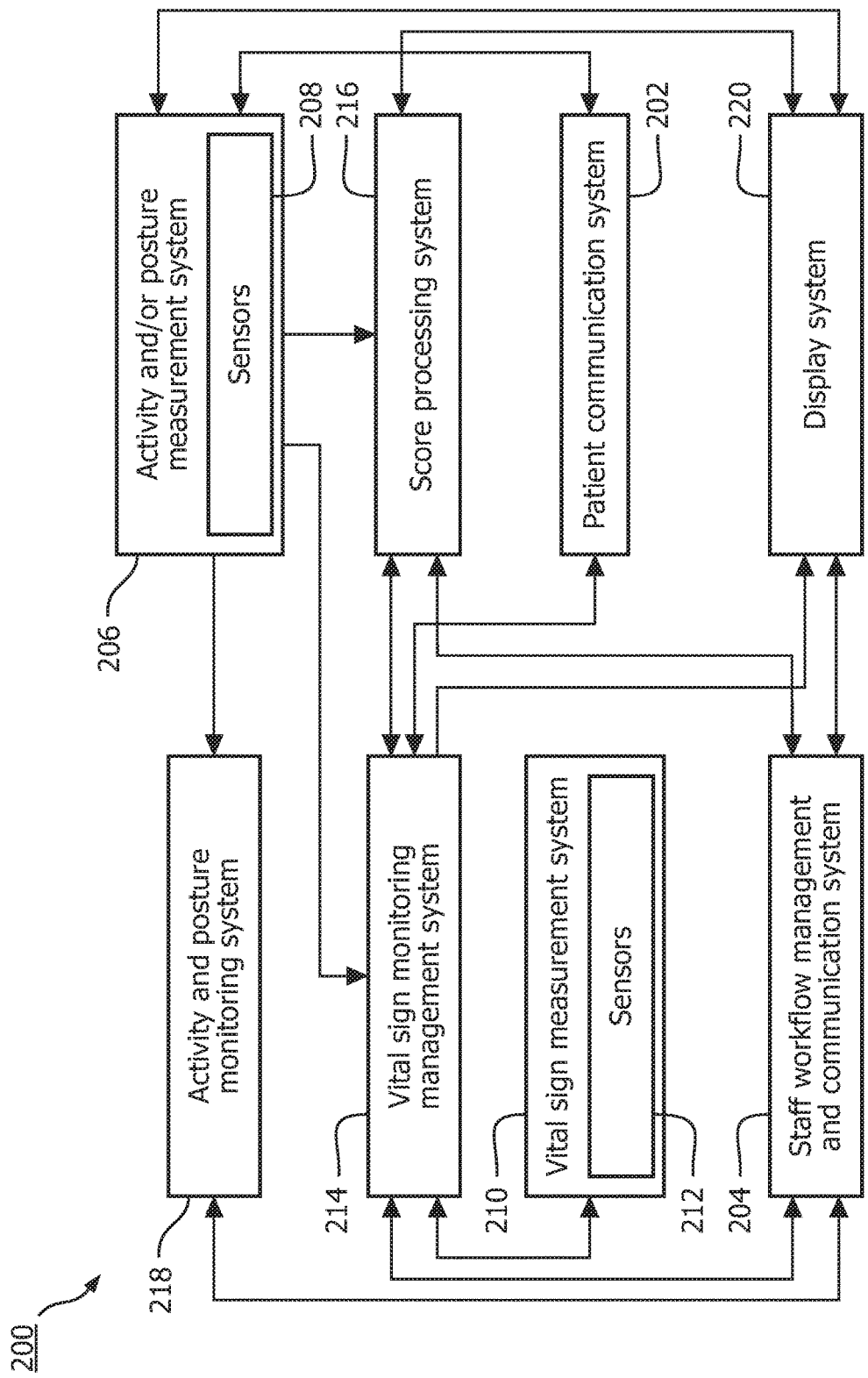
FIG. 12 illustrates an enhanced clinical workflow system.

With reference to FIG. 12, an enhanced clinical workflow system 200 is provided. The enhanced clinical workflow system 200 can be used in every environment where the patient state is assessed as a whole only intermittently and in-between additional measurements are taken automatically (unattended).

The enhanced clinical workflow system 200 includes a patient communication system 202 allowing unidirectional and/or bidirectional communication between the enhanced clinical workflow system 200 and an associated patient. The patient communication system 202 can be realized by, for example, a conventional display system, a touch-screen system, a sound playing system, a lighting system, a tactile interface system, or on a combination of any or all of such systems.

A staff workflow management and communication system 204 allows unidirectional and/or bidirectional communication between the enhanced clinical workflow system 200 and staff at a medical institution, such as a hospital, employing the enhanced clinical workflow system 200. Communication can be performed using, for example, one or more uni- or bi-directional communication means, such as audio systems, lighting systems, display systems, touch-screen systems, buzzer systems, etc. Further, the staff workflow management and communication system 204 allows modification of staff workflows. For example, the workflow of a nurse could be modified to increase the frequency of spot checks.

A patient activity state monitoring system 206 determines the activity state and/or posture of the patient. Activity state can include one or more of present and recent physical activity levels, physical activity types, sleep state(s), mental state(s), and so on. A primary example of an activity state is a resting state (i.e., a state in which a patient's vital signs are likely to reflect a baseline situation).

The activity state and/or posture can be determined automatically using one or more sensors 208 according to well-known techniques. For example, physical aspects of the activity state of the patient can be determined using motion sensing with, for example, accelerometry or video actigraphy. Mental aspects of the activity state can be determined using, for example, sleep detection methods, such as those based on electroencephalography (EEG). Additionally, the activity state and/or posture can be determined using the patient communication system 202 and/or the staff workflow management and communication system 204. For example, the activity state and/or posture may be obtained by means of automatic interaction with the patient (e.g., through an electronic questionnaire). As another example, the activity state and/or posture may be obtained from nurses performing spot checks.

A vital signs measurement system 210 automatically measures one or more vital signs using one or more sensors 212. These sensors 212 can overlap with the sensors 208 employed for determining activity state and/or posture. The vital signs can include, for example, one or more of pulse, oxygen saturation, respiration, non-invasive blood pressure, temperature and carbon dioxide. Measurements are typically performed periodically according to a schedule. For example, measurements can be performed periodically every hour.

A vital sign monitoring management system 214 performs spot checks on the patient (i.e., collects vital sign measurements). Vital sign measurements can be collected automatically from the vital signs measurement system, typically when the patient is in a predetermined range of activity state and/or posture. Vital sign measurements can also be collected from the staff workflow management and communication system 204, the patient communication system 202, or any other system of the enhanced clinical workflow system 200. For example, staff can be requested to provide vital signs measurement. Patient monitors can be used baseline vital sign measurements, and patient worn devices or individual observations by clinicians can be used for intermittent measurements.

A score processing system 216 estimates the patient condition based on all vital sign measurements received from the vital signs measurement system 210 (typically by way of the vital sign monitoring management system 214). For example, a score could be assigned to each vital sign and then the scores of the vital signs could be totaled to determine a total monitoring score indicative of the patient condition. In some instances, those vital signs deemed to have a high dependency on activity state and/or posture by an operator of the score processing system can be suppressed when activity state and/or posture are outside an acceptable range. Suppression of a vital sign can include, for example, using the last measurement taken when activity state and/or posture were within the acceptable range in place of the current measurement.

If the patient's score for one or more vital signs has become worse compared to the previous spot check, the score processing system 216 can automatically re-measure these vital signs (typically by way of the vital sign monitoring management system 214) after a delay, such as one or five minutes. Alternatively, if the patient's total score has become worse compared to the previous spot check, the score processing system 216 can automatically re-measure all the vital signs after a delay. In both cases, the delay can be set by a user of the score processing system 216 or set based on the activity state and/or posture of the patient.

As an alternative, the re-measurement can be delayed until activity state and/or posture (e.g., activity level) is within an acceptable range. Further, a measurement schedule safety net can be put in place to re-measure after a maximum amount of time has passed (i.e., an upper limit). The upper limit can be set by a user of the score processing system 200 or set based on the activity state and/or posture of the patient.

If after the re-measurement, the score (e.g., the total score or an individual vital sign score) shows deterioration, a notification of the deterioration is generated using the staff workflow management and communication system 204. For example, the notification can be displayed on a patient monitor, logged for subsequent review, or conveyed to a clinician caring for the patient. If activity state and/or posture are outside an acceptable range (e.g., activity level is above a predetermined threshold defined by an operator of the score processing system 204 as being indicative of high activity level), the notification can further include an activity state and/or posture constraint. Otherwise, the notification is unconstrained. Hence, there are two types of deterioration notifications (e.g., constrained and unconstrained deterioration notifications) to support caregiver assessment of patient acuity change. In some instance, if a notification for a certain severity of deterioration is generated under the activity state and/or posture constraint, a notification for a same severity deterioration could be announced again in a situation where activity state and/or posture are within an acceptable range.

Alternatively, if after the re-measurement, the score shows deterioration and the activity state and/or posture are outside an acceptable range, a notification can be generated indicating that due to activity state and/or posture a deterioration announcement is not reasonable using the staff workflow management and communication system 204.

An activity and posture monitoring system 218 monitors the activity state and/or posture of the patient and generates posture and/or activity notifications to clinicians using the staff communication and workflow system 204. Such notifications include posture and activity notifications. The notification can, for example, be displayed on a patient monitor, logged for subsequent review, or conveyed to a clinician caring for the patient.

Posture notifications can be generated periodically and include features extracted from a trend of posture over a predetermined period of time. Further, posture notifications can be generated if certain conditions are met. These conditions can be based on a combination of multiple (configurable) postures, typically lying positions.

For example, an activity notification can be generated if a patient has been in a position or subset of postures for more than a predetermined period of time (configurable by an operator of the activity and patient monitoring system 218). Examples of positions are shown in FIG. 20, described in more detail hereafter. Further, FIGS. 27-30 illustrate posture bars showing posture over time using the mapping of postures in FIG. 26. These figures are described in further detail below. After a certain amount of time within a configurable set or subset of postures (e.g., lying on left side), a notification can be generated.

As another example, a notification can be generated after a patient leaves one of these positions, the notification indicating how long the patient was in the position. As another example, a notification can be generated if rate of change to different positions exceeds a threshold. In some instances, notifications are delayed after a condition is met and only generated if the condition persists. An example of a posture notification can request that a clinician shift a patient position or care for the patient.

Posture notifications have to tolerate temporary moves to other positions of the patient to avoid unnecessary false notifications. Hence, the posture conditions can, for example, further include an absolute time range outside of expected position before generating a notification. For example, N Minutes outside the expected green positions must pass before generating an alarm. Alternatively, these conditions can include, for example, a relative time range over a configured amount of time outside the expected position before generating a notification. For example, x % (percentage) of time outside the expected position.

Activity notifications can be generated periodically and include features extracted from a trend of activity state over a predetermined period of time, such as sum of activity level, maximum activity level, peak values/time period and the like. Further, activity notifications can be generated if certain conditions are met based on these features or other features. For example, an activity notification can be generated if a patient has been at an activity state (e.g., activity level) for more than a predetermined period of time.

Figure 18:
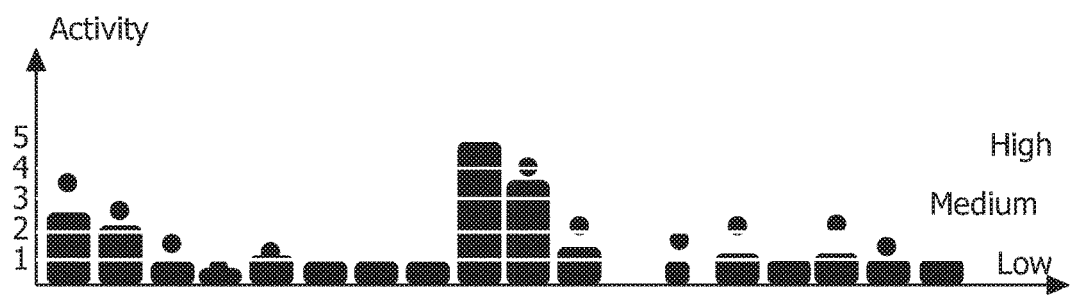
FIG. 18 illustrates an example of a horizontal trend line for activity level.

As another example, an activity notification can be generated if a patient has not reached a certain activity level over a predetermined period of time when, for example, the patient is expected to be out of bed walking (this can be seen in, for example, FIG. 18). As another example, an activity notification can be generated if an unexpected peak in activity level is detected when, for example, the patient is expected to have bed rest (this can be seen in, for example, FIG. 19). These two examples, and others, can be determined by translation of the trend line of FIGS. 18 and 19. More generally, FIGS. 18 and 19, described in detail below, can be translated to automatically generate activity notifications to the caregiver, because it cannot be assumed that the caregivers review the chart. Caregivers can be notified by paging or display.

Activity notifications have to tolerate temporary other/ unexpected activity levels of the patient to avoid unnecessary false notifications. Hence, the activity conditions can, for example, further include an absolute time range outside of expected activity level before generating a notification. For example, notify only after a predetermined amount of time (e.g., 10 minutes) of other/unexpected activity passes. Put another way, notifications are delayed after a condition is met and only generated if the condition persists. An example of an activity notification is a notification requesting that a clinician check the patient's exercise status if a condition persists for 10 minutes.

A display system 220 provides a consistent approach for visualizing the activity state and/or posture of the patient on a display device using, for example, the staff workflow management and communication system 204. A consistent presentation is important to allow the easy recognition of activity state and/or posture and the (implicit) recognition of which values are show (especially in small form factors). As described hereafter, visualization can be performed using display elements, such as icons and graphs. The display elements can be of variable size, but are more than shrunk or enhanced graphical images. Rather, the display elements become more abstract as they get smaller.

When displaying activity state, typically activity level is employed. Activity level can be displayed using a vertical or horizontal bar, the length of the bar spanning between two extremes, a first extreme and a second extreme. The first extreme represents the minimum activity level and/or unavailability of data on activity level (e.g., the sensors measuring activity state and/or posture are not attached to the patient), whereas the second extreme represents the maximum activity level. As the activity level increases, an increasing percentage of the bar is set from the first extreme to the second extreme. Setting a percentage of the bar includes coloring or otherwise visually modifying the portion to stand out from the remaining portion of the bar. Similarly, as the activity level decreases, a decreasing percentage of the bar is set from the first extreme to the second extreme.

Figure 13:
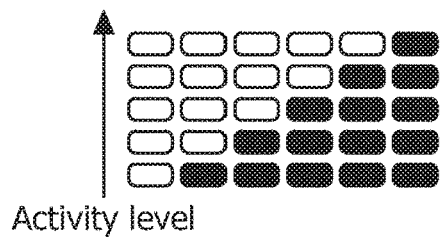
FIG. 13 illustrates an example of a vertical activity bar.

Referring to FIG. 13, an example is illustrated of using a vertical activity bar comprised of 5 display elements spaced between the two extremes of the length of the vertical bar. As the activity level increases, more and more elements are set (e.g., color or otherwise visually modified to distinguish from the unset elements). Similarly, as the activity level decreases, more and more elements are unset. The first (i.e., leftmost) column represents the bar with minimum activity level and/or the unavailability of data on activity level. The sixth column (i.e., the rightmost) column represent the bar with maximum activity level. The second through fifth columns represent the bar with increasing activity level. The vertical bar could also be used horizontally. Further, more or less elements could be employed.

Figure 14A:
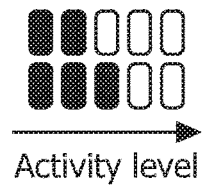
FIG. 14A illustrates examples of horizontal activity bars for two different activity levels.
Figure 14B:
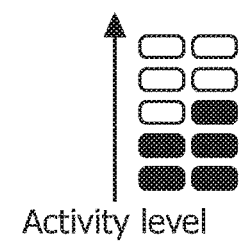
FIG. 14B illustrates examples of vertical activity bars for two different activity levels.
Figure 15A:
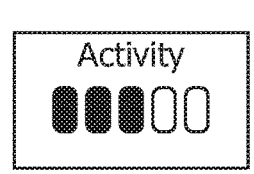
FIG. 15A illustrates an example display of horizontal activity level.
Figure 15B:
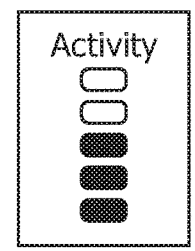
FIG. 15B illustrates an example display of vertical activity level.

Referring to FIGS. 14A and 14B, horizontal and vertical activity bars are shown. FIG. 14A illustrates two horizontal bars, each set for a different activity level. FIG. 14B illustrates two vertical bars, each set for a different activity level. Referring to FIGS. 15A and 15B, a horizontal and vertical display of activity level, respectively, is illustrated.

Figure 16:
FIG. 16 illustrates an example of the numeric display of activity level.

Another approach for displaying activity level is to display activity level using a numeric value representing the activity level of the patient. The numeric value can range from a first extreme to a second extreme, the first extreme indicating the minimum activity level and/or unavailability of data on activity level, and the second extreme indicating the maximum activity level. For example, the numeric value can range from 0 to 5, where zero indicates the unavailability of data, 5 indicates the maximum activity level, and from the 0 to 5 representing increasing activity levels. Referring to FIG. 16, the numeric display of activity level is illustrated.

Figure 17A:
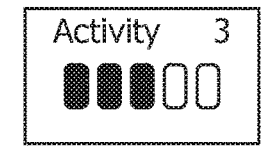
FIG. 17A illustrates an example of a horizontal activity bar and the corresponding numeric value.
Figure 17B:
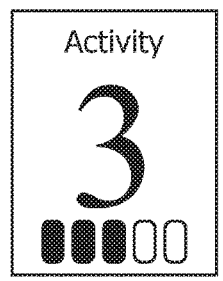
FIG. 17B illustrates another example of a horizontal activity bar and the corresponding numeric value.
Figure 17C:
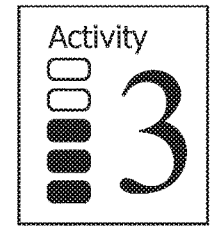
FIG. 17C illustrates an example of a vertical activity bar and the corresponding numeric value.

Yet another approach for display activity level is to display activity level as a combination of the activity bar approach and the numeric value approach described above. For example, referring to FIGS. 17A-C, three example displays are illustrated. FIGS. 17A and 17B illustrate a horizontal activity bar and the corresponding numeric value. FIG. 17C illustrates a vertical activity bar and the corresponding numeric value.

To assist in the process of attaching the sensors measuring activity state and/or posture to the patient, the activity numeric and/or bar can be updated in real-time or near real-time. For example, the activity numeric and/or bar can be updated every second. It may even be helpful to show a trend of the activity numeric and/or bar with, for example, one second intervals.

Activity level can be shown on a vertical or horizontal trend line using the activity bar described above as shown, for example, in FIG. 18. When the trend line is vertical, horizontal activity bars are used. Similarly, when the trend line is horizontal, vertical activity bars are used. An activity bar is added to the trend line every predetermined period of time, such as every 10 seconds. Each activity bar represents the interval spanning from the previous activity bar to the activity bar. For example, the activity bar can represent the average, maximum or minimum activity level over the interval.

Intervals during which data on activity level is unavailable have no activity bar. Activity bars corresponding to intervals during which the activity level was unavailable or partially unavailable can be shown with augmented appearances. For example, such activity bars can be shown lighter, such as with half of the usual width, as illustrated by [h], [k], and [n] in FIG. 19. As another example, such activity bars can be shown with a lighter shade of color (e.g., grey compared to black), as illustrated by [g] and [m] in FIG. 19, or just shown with their outline and no filling, as illustrated by [f] and [l] in FIG. 19.

In some instance, it is advantageous to show both the maximum activity level and average activity level. For example, average activity level can be displayed as described above and maximum activity level can be displayed by a dot, cross or fine vertical line, as illustrated by [b], [c], and [d] in FIG. 19. Typically, both maximum and average activity level for an interval are display using the same visual style (e.g., color, pattern, etc.).

As illustrated in FIG. 18, maximum activity level is shown by a dot. Displaying both the maximum activity level and average activity level helps to distinguish intervals during which the patient was at rest (e.g., sleeping) for a long time and intervals during which the patient stayed in bed or sat on a chair (e.g., low average activity level), but got up and was moving around. As to the former, the average activity level is low and no dot is visible because the max and average activity levels are basically the same. As to the latter, the dot corresponds to a value much higher than average. In the middle section of FIG. 7, the patient continuously exercised (i.e., high activity level and no dot) and then started to pause in the following intervals. The average activity level was still high, but the maximum activity level was higher (i.e., there were times with less activity).

Further, in some instances, it is advantageous to show average, 90% and maximum activity levels. For example, average and maximum activity level can be displayed as described above and 90% activity level can be displayed lighter, such as with half of the usual width, as illustrated by

Figure 19:
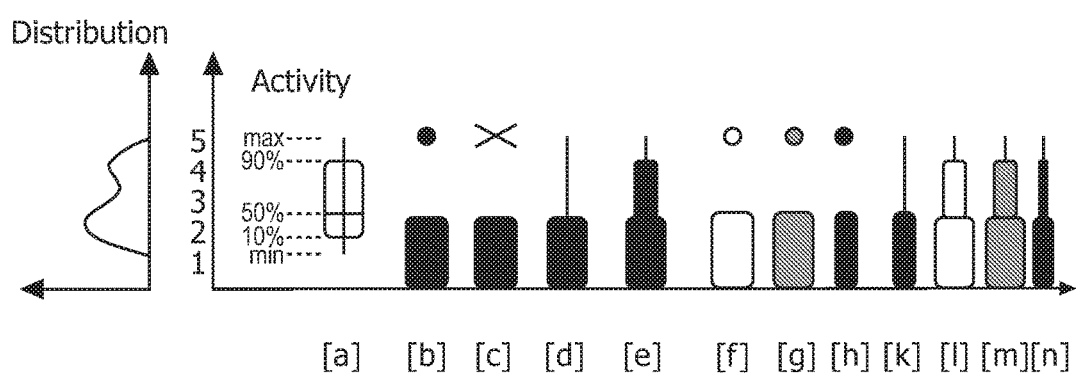
FIG. 19 illustrates different approaches to displaying an activity bar on a trend line.

[e], [l], [m] and [n] in FIG. 19. Typically, average, 90% and maximum activity levels for an interval are displayed using the same visual style (e.g., color, pattern, etc.).

There is typically no clinical need to show the minimum value or the 10% value, as done with conventional style, an example of which is illustrated by [a] in FIG. 19. It typically just data clutter. Showing only the average and maximum value (shown by [b], [c], [d], [f], [g], [h] and [k] in FIG. 19) or average, 90% and maximum value (shown by [e], [1], [m], n] in FIG. 19) is more appropriate. Nonetheless, it is to be appreciated that the 10% value and/or the minimum value can additionally be displayed using the techniques described (e.g., using different widths) and/or in place of at least one of the average, 90% and maximum values.

Posture can be displayed with one or more of a key word or phrase describing the posture (e.g., supine), an icon or using a combination. Referring to FIG. 20, a table illustrates key words or phrases and corresponding icons that can be used to describe posture. The above postures are static (i.e., they can be derived instantaneously from sensor measurements, such as accelerometer measurements). FIGS. 21A and 21B illustrate two displays of posture. FIG. 21A displays both an icon and keyword or phrase, whereas FIG. 21B displays only an icon.

Dynamic posture can also be displayed. Dynamic posture takes in to account the sequence and timing of posture changes. Referring to FIG. 22, a table illustrates key words or phrases and corresponding icons that can be used to describe dynamic posture. Other key words or phrases that can be used include "going up stairs", "going down stairs", "falling" and "bed leave".

In some instances, a new posture is displayed only after a threshold in time and/or change in position (e.g., angle) has been crossed. This avoids changing the displayed position if a measurement is in between two positions or the position is not yet stable. If a position is unstable for a prolonged time, a specific position of "unstable" can be displayed.

Posture can be displayed as a single key word or phrase or icon that is constantly updated. Alternatively, posture can be shown using a list with timestamps, and key words or phrases and/or icons, as illustrated in FIGS. 23A and 23B. FIG. 23A illustrates a list of keywords or phrases, and FIG. 23B illustrates a list of icons. Posture can also be displayed on a timeline using icons, as illustrated in FIG. 24.

Figure 25A:
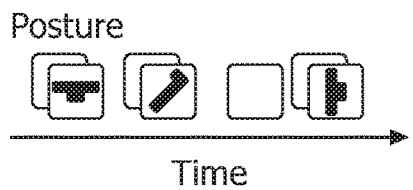
FIG. 25A illustrates an example timeline using groupings of icons to indicate a plurality of icons.
Figure 25B:
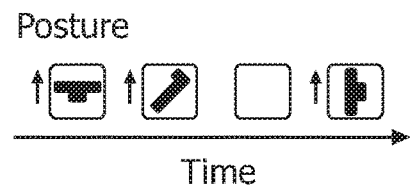
FIG. 25B illustrates an example timeline using arrows to indicate a plurality of icons.
Figure 25C:
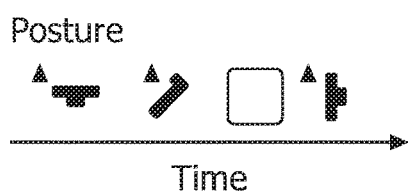
FIG. 25C illustrates another example timeline using arrows to indicate a plurality of icons.
Figure 25D:
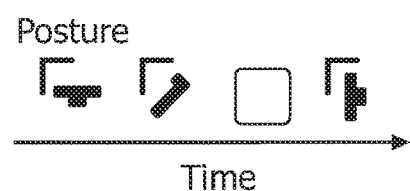
FIG. 25D illustrates another example timeline using an abstract symbol to indicate a plurality of icons.
Figure 25E:
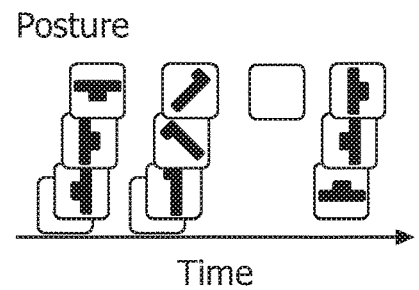
FIG. 25E illustrates another example timeline using staggered icons in a direction perpendicular to the time axis to indicate a plurality of icons.

A timeline of icons for, for example, posture may need to be compressed along the time axis, usually horizontally, due to space limitations (e.g., for showing a longer time period). One approach for doing this is to use a graphical language that indicates more icons, examples of which are shown in FIGS. 25A-E. The groupings of icons shown in FIG. 25A indicate a plurality of icons that can be expanded upon selection. The arrows in FIGS. 25B and 25C indicate a plurality of icons that can be expanded upon selection of the corresponding icon. More abstract symbols can be used in lieu of arrows, as shown in FIG. 25D. Icons can also be staggered in another dimension (e.g., a direction perpendicular to the time axis), as illustrated in FIG. 25E.

Figure 26:
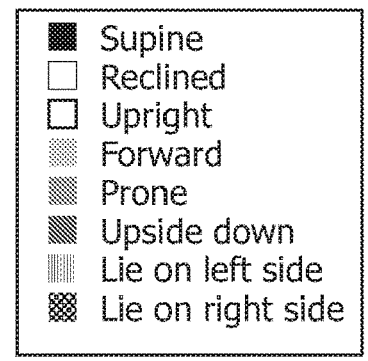
FIG. 26 illustrates a mapping between postures and visual styles.
Figure 27:
FIG. 27 illustrates an example posture bar.

For reviewing the patient's posture, especially if patient has to be moved periodically, a more intuitive approach for displaying posture is to map possible postures to different visual styles (e.g., color, pattern, etc.) and display a bar of the different visual styles representing the different postures. For example, "supine", "reclined", "upright", "forward", "prone", "upside down", "lie on left side" and "lie on right side" can be mapped to different colors, as shown in FIG. 26. A bar of these visual styles can then be displayed, as shown in FIG. 27.

Another approach is to employ a vertical or horizontal bar, the latter typically better if timing aspects are included. In this approach, the possible postures are mapped to different visual styles (e.g., color, pattern, etc.), as above. The bar is displayed with a plurality of different regions extending between the extremes of the length of the bar, each region corresponding to a different posture detected during a time window represented by the bar. Further, each region is displayed with the visual styles of the corresponding posture and sized to fill the percentage of the bar corresponding to the percentage of time the patient was in the corresponding posture during the time window. The width of the time window can, for example, be fixed, configurable or arbitrary.

Figure 28:
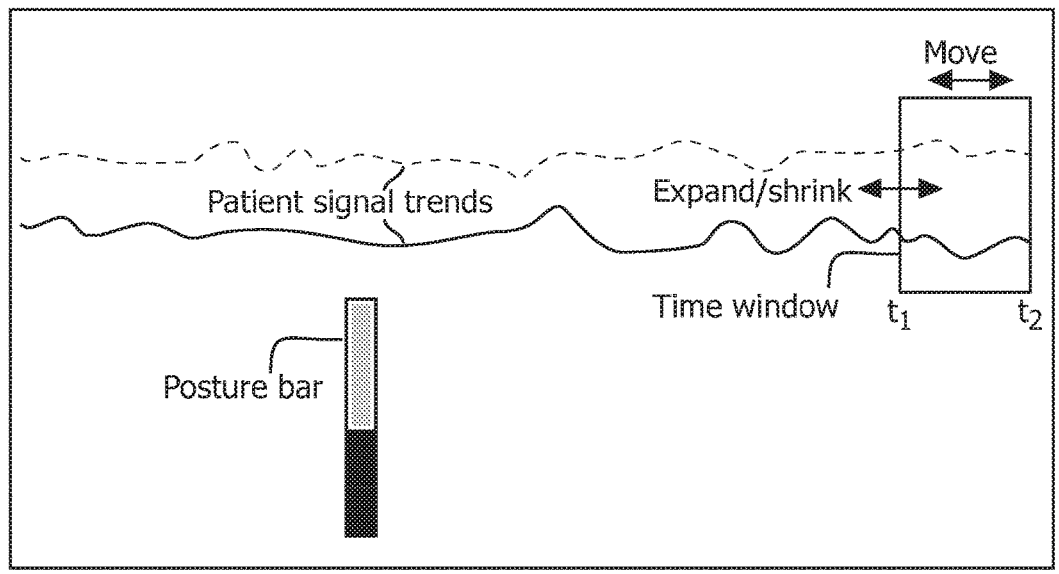
FIG. 28 illustrates an example of the movement of a time window for a posture bar.

Further, the time window can be moved, for example, smoothly or in fixed time steps. For example, the bar can be displayed adjacent the trend lines for one or more vital signs (e.g., respiration rate) and a graphical representation of the time window can be overlaid on the corresponding portion of the trend line. This example is illustrated FIG. 28. As illustrated in FIG. 28, a vertical bar for posture is provided, as well as the patient signal trends for a plurality of vital signs and the time window corresponding to the vertical bar. The patient was in a first posture (e.g., on their right side) for 60% of the time window spanning from $t_1$ to $t_2$ and a second posture (e.g., on their left side) for 40% of the time window.

The posture bar described in FIG. 28 lacked timing information. The patient could have been in the first posture (e.g., on their right side) for 30% of the time, then in the second posture (e.g., on their left side) for 40% of the time, and then in the first posture for another 30% of the time. One approach to displaying timing information is to use the length of the posture bar as a time axis, the extremes of the length representing the extremes of the time window. The postures detected during the time window are then displayed in the corresponding time regions using the corresponding visual styles, as illustrated in FIG. 27.

Figure 29:
FIG. 29 illustrates an example posture bar using sorting.

Displaying the timing information in the posture bar as done in FIG. 27 above could make it look very diffuse if the patient moves a lot. To improve the display of timing information, the detected postures can be sorted by average age of their occurrence relative to the beginning of the time window. The postures can then be displayed as sorted. FIG. 29 illustrates a posture bar using this approach for displaying timing information. The patient was in a first posture (e.g., on their right side) for 60% of the time window and in a second posture (e.g., on their left side) for 40% of the time window. However, most recently the patient was in the first posture. In other words, the average age of the occurrences of the first posture relative to the beginning of the time window is greater than the average age of the occurrences of the second posture. Hence, the first posture is displayed after the second posture in the posture bar.

Figure 30:
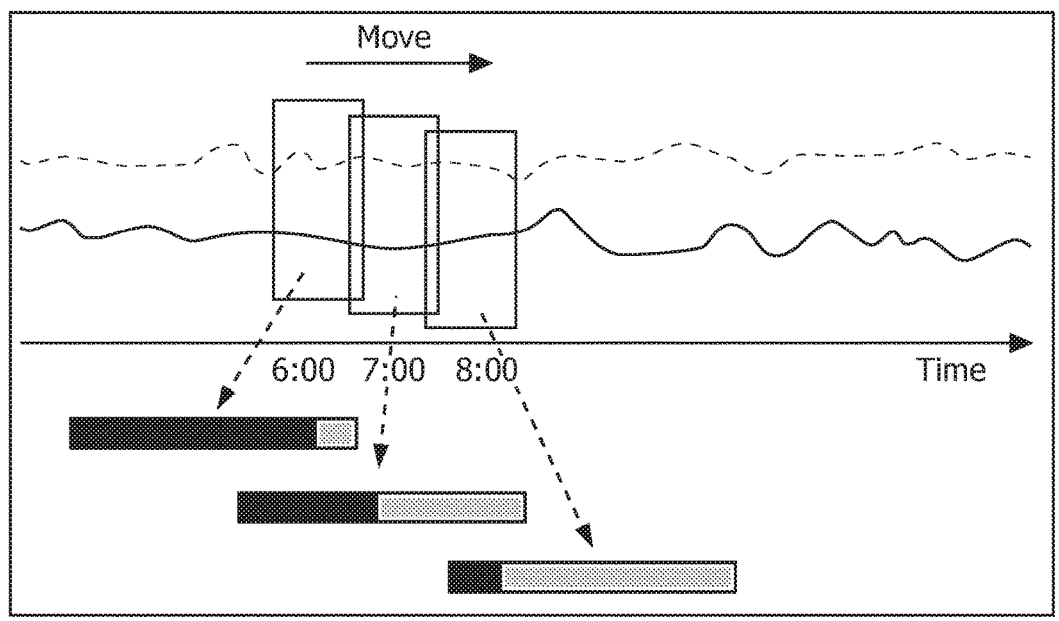
FIG. 30 illustrates an example of estimating events by moving the time window and reviewing the change in the posture bar.

The posture bar with time sorting allows estimating events by moving the time window and reviewing the change in the posture bar. An example of this is illustrated in FIG. 30. In this example, the patient was moved from a first position (e.g., on their left side) to a second position (e.g., on their right side) at 7:00. In this example, if the first posture was "reclined" and the second posture was "supine", the patient might have gone to sleep.

Both activity state and posture can be relevant when judging other vital signs (e.g., heart rage or non-invasive blood pressure). To indicate activity state and/or posture while taking a measurement of another vital sign and/or shortly before taking the measurement, a representation (typically small) of activity state and/or posture can be displayed proximate the measurement. The activity state and/or posture are relevance indicators when displayed proximate a measurement.

Figure 31A:
FIG. 31A illustrates an example of a relevance indicator while a patient is supine.
Figure 31B:
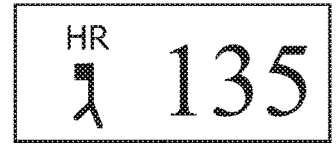
FIG. 31B illustrates an example of a relevance indicator while a patient is walking.
Figure 32:
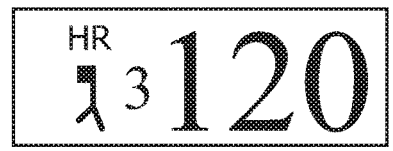
FIG. 32 illustrates an example of a relevance indicator including both activity level and posture.

For example, as shown in FIGS. 31A and 31B, a patient had a heart rate of 90 while lying supine (FIG. 31A) and a heart rate of 135 while walking (FIG. 31B). As another example, as shown in FIG. 32, a patent has a heart rate of 120 while walking and a medium (3) activity level.

Figure 33:
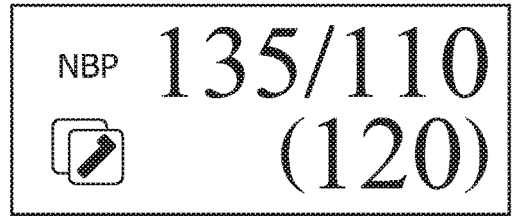
FIG. 33 illustrates an example of using of the compressed form of posture for display as a relevance indicator.
Figure 34A:
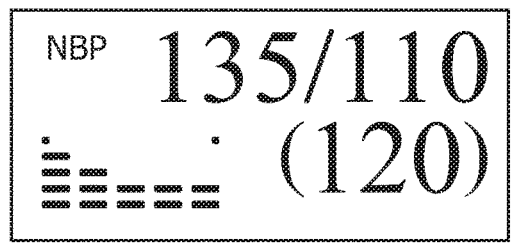
FIG. 34A illustrates an example of using a trend for activity level as a relevance indicator.
Figure 34B:
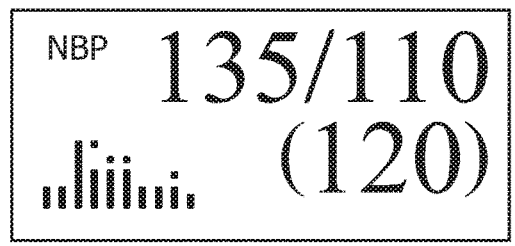
FIG. 34B illustrates another example of using a trend for activity level as a relevance indicator.

For the relevance indicator, all, preferably small, presentation styles described above can be used. For example, for posture, the compressed form (e.g., arrows, groupings, or stacked or any combination could be used) can be employed, as illustrated in FIG. 33. The interval of a relevance indicator (e.g., for activity state and/or posture), such as 5 or 10 minutes, is implicit from the spot check frequency for the corresponding vital sign. A small presentation of a trend of activity state and/or posture, such as a minimum-value trend, can be employed as well, examples of which are illustrated in FIGS. 34A and 34B.

The patient preparation system 10, the adaptive patient monitoring system 100, and the enhanced clinical workflow system 200 can be used individually or in combination with each other. For example, the patient preparation management system 100 can be employed to collected vital sign measurements and the adaptive patient monitoring system 100 can be employed to adjust the measurement frequencies. The enhancements, such as the display system 220 for displaying patient activity state and/or posture, can further be added.

Further, the functionality of the patient preparation system 10, the adaptive patient monitoring system 100, and the enhanced clinical workflow system 200 can each be implemented in hardware, software or a combination of the two. When software is involved with one of the patient preparation system 10, the adaptive patient monitoring system 100, and the enhanced clinical workflow system 200, the system 10, 100, 200 includes one or more program memories with processor executable instructions embodying the relevant functionality and one or more processors executing the processor executable instructions.

Even more, notifications can be presented to staff (e.g., clinicians) by way of any uni- or bi-direction communication means. For example, data can be presented to staff by way of a display device, and data can be received by staff using a user input device. The display device can optionally be used to display an interface to facilitate the receipt of data from staff.

Figure 35:
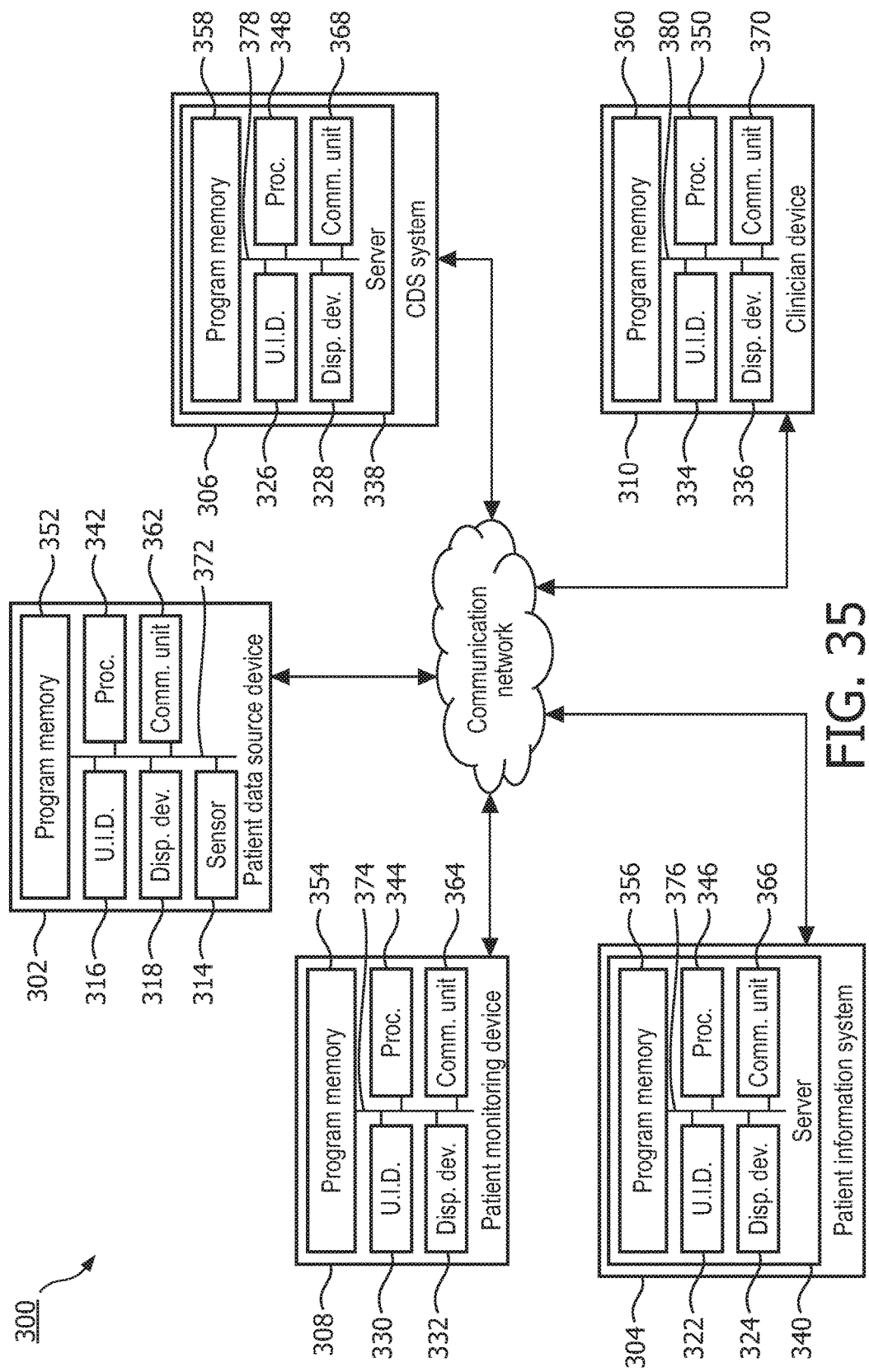
FIG. 35 illustrates an example of a medical system within which a patient preparation system, an adaptive patient monitoring system, and an enhanced clinical workflow system can be employed.

With reference to FIG. 35, a medical system 300 of a medical institution, such as a hospital, within which the patient preparation system 10, the adaptive patient monitoring system 100, and the enhanced clinical workflow system 200 can be employed is illustrated. The medical system 300 includes one or more patient data source devices 302, optionally a patient information system 304, a clinical decision support (CDS) system 306, one or more patient monitoring devices 308 and one or more clinician devices 310. Suitably, the components of the medical system 300 are interconnected through a communication network 312, such as the Internet, a local area network, a wide area network, a wireless network, or the like.

The patient data source devices 302 generate patient data for corresponding patients. The patient data suitably includes vital sign measurements for, for example, heart rate, temperature, blood oxygen saturation (SpO2), level of consciousness, concern, pain, urine output, and so on. The patient data can also include data indicative of activity state and/or posture. The patient data can be generated automatically and/or manually. As to the former, one or more sensors 314 of the patient data source devices 302, such electrocardiographic (ECG) electrodes, blood pressure sensors, SpO2 sensors, accelerometers, and so on, can be employed to measure the vital signs, as well as activity state and/or posture. As to the latter, one or more user input devices 316 can be employed, optionally in conjunction with one or more display devices 318 providing users a user interface within which to manually enter the patient data. The user input devices 316 can also be employed to configure the patient data source devices 302. Examples of patient data source devices include, but are not limited to, patient monitors, nursing stations, mobile communications devices, cableless measurement devices, patient information systems, and so on.

One or more of the patient preparation system 10, the adaptive patient monitoring system 100, and the enhanced clinical workflow system 200 can be implemented partially or wholly in one or more of the patient data source devices 302. For example, one or more of the activity and/or posture measurement system 26, the vital sign monitoring management system 38, the patient preparation management system 40 and the vital sign measurement system 34 of FIG. 1 can be implemented in one or more of the patient data source devices 302. As another example, one or more of the vital sign measurement system 102, the score processing system 108, and the monitoring frequency control system 110 of FIG. 8 can be implemented in one or more of the patient data source devices 302. As another example, one or more of the activity and/or posture measurement system 206, the vital sign monitoring management system 214, and the vital sign measurement system 210 of FIG. 12 can be implemented in one or more of the patient data source devices 302.

The patient information system 304 stores patient data from the medical system 300, such as from the patient data source devices 302, in one or more databases. For example, the patient information system 304 can store respiration rate for a patient from one of the patient data source devices 302. In some instances, the patient information system 304 also stores patient data from a user input device 322 of the patient information system 304 in the databases and/or allows stored patient data to be viewed on a display device 324 of the patient information system 304. The display device 324 can additionally or alternatively be used to facilitate receipt of data from the user input device 322. Examples of patient information systems include, but are not limited to, electronic medical record systems, departmental systems, and the like.

The CDS system 306 receives patient data. The patient data is typically received from other systems of the medical system 300 (e.g., the patient data source devices 302 and/or the patient information system 304), but can also be received from a user input device 326 of the CDS system 306. The user input device 326 can also be used to configure the CDS system 306. A display device 328 of the CDS system 306 can additionally be used to facilitate receipt of data from the user input device 326.

Using the patient data, the CDS system 306 typically monitors for patient deterioration, for example, using a scoring system. In response to detecting patient deterioration, alerts are generated and conveyed to clinicians (e.g., using a communication system and/or the patient monitoring devices 308). The CDS system 306 can also distribute patient data to other systems of the medical system 300. For example, the CDS system 306 can provide the patient data to the patient information system 304 for storage. As another example, the CDS system 306 can convey patient data to the patient monitoring devices 308.

One or more of the patient preparation system 10, the adaptive patient monitoring system 100, and the enhanced clinical workflow system 200 can be implemented partially or wholly in the CDS system 306. For example, at least the workflow functionality of the staff workflow management and communication systems 24, 106, 204 of FIGS. 1, 8 and 12, respectively, can be implemented in the CDS system 306. As another example, the monitoring frequency control system 110 can be implemented across the CDS system 306 and one or more of the patient data source devices 302, with the CDS system 306 adjusting monitoring frequency based on acuity level and/or manual spot check frequency set for each patient and with the one or more of the patient data source devices 302 adjusting monitoring frequency based on score. As another example, one or more of the score processing system 216, the activity posture monitoring system 218, the score processing system 216, and the vital sign monitoring management system 214 can be implemented in the CDS system 306.

The patient monitoring devices 308 monitor patient data and one or more of: 1) generate notifications of clinically significant conditions in response to the patient data; and 2) display the patient data or derived scores. The patient data is typically received from other systems of the medical system 300 (e.g., the patient data source devices 302 and/or the patient information system 304), but can also be received from user input devices 330 of the patient monitoring devices 308 or local sensors (e.g., a patient monitoring device can be the same as a patient data source device). The user input devices 330 an also be used to configure the patient monitoring devices 308. Display devices 332 of the patient monitoring devices 308 can additionally be used to facilitate receipt of data from the user input devices 330. Notifications can be displayed on the display devices 330, conveyed to clinicians using a communication system, conveyed to other systems of the medical system (e.g., the CDS system 306), or stored internally on a storage memory.

One or more of the patient preparation system 10, the adaptive patient monitoring system 100, and the enhanced clinical workflow system 200 can be implemented partially or wholly in one or more of the patient monitoring devices 308. For example, one or more of the activity and/or posture measurement system 26, the vital sign monitoring management system 38, the patient preparation management system 40 and the vital sign measurement system 34 of FIG. 1 can be implemented in one or more of the patient monitoring devices 308. As another example, one or more of the vital sign measurement system 102, the score processing system 108, and the monitoring frequency control system 110 of FIG. 8 can be implemented in one or more of the patient monitoring devices 308. As another example, one or more of the activity and/or posture measurement system 206, the vital sign monitoring management system 214, the vital sign measurement system 210, the display system 220, and the score processing system 216 of FIG. 12 can be implemented in one or more of the patient monitoring devices 308.

The clinician devices 310 receive and display notifications and/or patient data. from the medical system 300. The notifications and/or the patient data are typically received from other systems of the medical system 300 (e.g., the patient data source devices 302 and/or the patient information system 304). User input devices 334 can be used to communicate with other systems of the medical system 300 and/or to configure the clinician device 310. Display devices 336 of the clinician devices 310 can additionally be used to facilitate receipt of data from the user input devices 334. CDS client devices include pagers, smart phones, patient monitors, tablet PCs, mobile clinical assistants, laptops, workstations, and so on.

One or more of the patient preparation system 10, the adaptive patient monitoring system 100, and the enhanced clinical workflow system 200 can be implemented partially or wholly in one or more of the patient monitoring devices 308. For example, the display system 220 of FIG. 12 can be implemented one of the clinician devices 310.

Each of the patient information system 304 and the CDS system 306 include at least one server 338, 340. Communication between the at least one server 338, 340 can be performed over a communication network, such as the communication network 312 of the medical system 300. At least some of the components of the medical system 300 each include at least one processor 342, 344, 346, 348, 350 executing computer executable instructions from at least one program memory 352, 354, 356, 358, 360 thereof. Components include the patient data sources 302, the at least one server 338, 340, the patient monitoring devices 308, and the clinician devices 310. The computer executable instructions embody the functionality of the components.

Further, at least some of the components each include a communication unit 362, 364, 366, 368, 370 and/or at least one system bus 372, 374, 376, 378, 380. A communication unit provides a corresponding processor with an interface to at least one communication network, such as the communication network 312. A system bus allows the exchange of data between sub-components of the components. Sub-components include processors, memories, sensors, display devices, communication units, and so on.

As used herein, a memory includes one or more of a non-transient computer readable medium; a magnetic disk or other magnetic storage medium; an optical disk or other optical storage medium; a random access memory (RAM), read-only memory (ROM), or other electronic memory device or chip or set of operatively interconnected chips; an Internet/Intranet server from which the stored instructions may be retrieved via the Internet/Intranet or a local area network; or so forth. Further, as used herein, a processor includes one or more of a microprocessor, a microcontroller, a graphic processing unit (GPU), an application-specific integrated circuit (ASIC), a field-programmable gate array (FPGA), and the like; a controller includes: 1) at least one memory with processor executable instructions to perform the functionality of the controller; and 2) at least one processor executing the processor executable instructions; a user output device includes a printer, a display device, and the like; and a display device includes one or more of a liquid crystal display (LCD), an light-emitting diode (LED) display, a plasma display, a projection display, a touch screen display, and the like.

The invention has been described with reference to the preferred embodiments. Modifications and alterations may occur to others upon reading and understanding the preceding detailed description. It is intended that the invention be constructed as including all such modifications and alterations insofar as they come within the scope of the appended claims or the equivalents thereof.

The invention claimed is:

1. A medical system comprising:
   at least one sensor configured to measure at least one of an activity state and a posture of a patient;
   at least one vital sign sensor separate from the at least one sensor and configured to measure one or more vital signs of the patient according to a schedule wherein the one or more vital signs comprise one or more of pulse, oxygen saturation (SpO2), respiration, temperature, and carbon dioxide;

at least one processor programmed to:
- adjust the schedule when the measured one or more vital signs is outside of a vital sign threshold;
- control the at least one vital sign sensor to measure the at least one vital sign according to the adjusted schedule including delaying a scheduled measurement until the activity state indicates a resting state that is below the position threshold;
- generate a patient deterioration alert when (i) the measured at least one of activity state and posture of the patient and (ii) the measured one or more vital signs are each outside of respective alarm thresholds; and
- output the patient deterioration alert to an audio device.

2. The medical system according to claim 1, wherein the schedule includes a measurement frequency for each of the one or more vital signs, and wherein the at least one processor is further programmed to:
- determine a patient deterioration score for each of the one or more vital signs from corresponding vital sign measurements;
- adjust the measurement frequency for each of the one or more vital signs based on changes in the corresponding patient deterioration score; and
- control the at least one vital sign sensor to measure the at least one vital sign with the adjusted frequency.

3. The medical system according to claim 2, wherein the at least one processor is further programmed to:
- determine a cumulative deterioration patient score from the one or more patient deterioration scores of the one or more vital signs; and
- at least one of:
  - adjust the measurement frequency for each of the one or more vital signs based on the cumulative deterioration patient score; and
  - adjust an individual scoring scheme of the patient deterioration scores including adjusting the vital sign thresholds and a list of measured vital signs.

4. The medical system according to claim 1, wherein the at least one processor is further programmed to:
- determine a patient deterioration score from the vital sign measurements;
- determine changes in the patient deterioration score,
- in response to a change in the patient deterioration score, re-measure one or more vital signs to confirm the change;
- in response to confirmation of the change and based on the change, adjust the schedule;
- control the at least one vital sign sensor to monitor the one or more vital signs according to the adjusted schedule.

5. The medical system according to claim 4, wherein the at least one processor is further programmed to:
- control the at least one vital sign sensor to measure the one or more vital signs;
- receive the one or more measured vital signs from the at least one vital sign sensor; and
- delay re-measuring of the one or more vital signs until the at least one of the activity state and the posture matches at least one of a predetermined activity state and posture.

6. The medical system according to claim 4, wherein the at least one processor is further programmed to:
- in response to confirmation of the change and based on the change, generate a notification.

7. The medical system according to claim 1, wherein the at least one processor is further programmed to:
- receive the one or more measured vital signs from the at least one vital sign sensor; and
- instruct the patient to take a predetermined at least one of an activity state and a posture before measuring one or more vital signs.

8. The medical system according to claim 1, wherein the at least one processor is further programmed to:
- control the at least one vital sign sensor to measure the one or more vital signs;
- receive the one or more measured vital signs from the at least one vital sign sensor; and
- discard vital sign measurements made when at least one of the corresponding activity state and the posture does not match a corresponding one of a predetermined activity state and a predetermined posture.

9. The medical system according to claim 1, wherein the at least one processor is further programmed to:
- receive the one or more measured vital signs from the at least one vital sign sensor; and
- display a vital sign measurement and the corresponding at least one of activity state and posture, the corresponding at least one activity state and posture displayed adjacent the vital sign measurement.

10. The medical system according to claim 1, wherein the at least one processor is further programmed to:
- calculate a posture trend;
- compare the posture trend to an expected posture trend; and
- display an indication of at least one of, based on the posture trend:
  - that the posture trend is as expected;
  - that the posture trend is not as expected; and
  - that action should be taken, such as turning the patient.

11. A medical method comprising:
- with a first sensor, measuring at least one of an activity state and a posture of a patient;
- with a second, separate sensor, measuring one or more vital signs of the patient according to a schedule;
- with at least one electronic processor, controlling the first and second sensors to continue the measuring operations when (i) the measured at least one of activity state and posture of the patient is inside of a position threshold and (ii) the measured one or more vital signs is inside of a vital sign threshold;
- with at least one electronic processor, adjusting the schedule when the measured one or more vital signs is outside of a vital sign threshold;
- with the at least one processor, controlling the second sensor to measure the one or more vital signs according to the adjusted schedule;
- with the at least one processor, generating a patient deterioration alert when (i) the measured at least one of activity state and posture of the patient and (ii) the measured one or more vital signs are both outside of an alarm threshold; and
- with the at least one processor, outputting the patient deterioration alert to an audio device.

12. The medical method according to claim 11, wherein the schedule includes a measurement frequency for each of the one or more vital signs, and wherein said medical method further includes:
- determining a patient deterioration score for each of the one or more vital signs from corresponding vital sign measurements; and adjusting the measurement frequency for each of the one or more vital signs based on changes in the corresponding patient deterioration score.

13. The medical method according to claim 11, further including:
   determining a patient deterioration score from the vital sign measurements;
   determining changes in the patient deterioration score,
   in response to a change in the patient deterioration score, controlling the second sensor to re-measure the one or more vital signs to confirm the change; and
   in response to confirmation of the change and based on the change, adjusting the schedule.

14. The medical method according to claim 13, further including:
   controlling the second sensor to delay re-measurement of the one or more vital signs until at least one of the activity state and posture matches a corresponding predetermined activity state and a posture.

15. The medical method according to claim 13, further including:
   in response to confirmation of the change and based on the change, generating a notification.

16. The medical method according to claim 11, further including:
   controlling an output device to delay an output of an indication requesting a clinician to instruct the patient to take a predetermined activity state or posture before measuring one or more vital signs.

17. The medical method according to claim 11,
   wherein when a corresponding at least one of an activity state and a posture does not match at least one of a predetermined activity state and posture, at least one of:
      discarding vital sign measurements made;
      delaying a scheduled measurement until the at least one of the activity state and the posture matches at least one of a predetermined activity state and a posture;
      adjusting the schedule; and
      generating the patient deterioration alert.

* * * * *